United States Patent [19]

Onishi et al.

[11] Patent Number: 4,603,208

[45] Date of Patent: Jul. 29, 1986

[54] CERTAIN POLYPRENYL INTERMEDIATES

[75] Inventors: Takashi Onishi; Shigeaki Suzuki; Fumio Mori; Tetsuo Takigawa; Yoshiji Fujita; Masao Mizuno; Takashi Nishida, all of Kurashiki, Japan

[73] Assignee: Kuraray Co., Ltd., Kurashiki, Japan

[21] Appl. No.: 465,483

[22] Filed: Feb. 10, 1983

[30] Foreign Application Priority Data

Feb. 11, 1982 [JP] Japan .................. 57-20855
Feb. 11, 1982 [JP] Japan .................. 57-20856

[51] Int. Cl.$^4$ ............. C07D 213/71; C07C 69/767; C07C 69/78; C07C 147/103
[52] U.S. Cl. ........................... 546/294; 546/268; 546/340; 546/344; 546/283; 546/284; 548/146; 560/106; 560/254; 568/28; 568/32; 568/41; 568/55; 549/14; 549/22; 549/30; 549/39; 549/374; 549/375; 549/416; 549/453; 556/427; 556/428
[58] Field of Search .............. 568/32, 28, 41, 55; 546/344, 294, 340, 268, 283, 284; 548/146; 549/416, 22, 14, 30, 39, 374, 375, 453; 556/427, 428; 560/254, 106

[56] References Cited

PUBLICATIONS

"Dolichol: A Naturally Occurring Isoprenoid Alcohol", Pennock et al., Nature, vol. 186, No. 4723, pp. 470–472, May 1960.
"The High–Performance Liquid–Chromatographic Analysis of Ficaprenol and Dolichol", Keenan et al., Biochem. J. vol. 165, pp. 405–408, (1977).
Biochemical and Biophysical Research Communications, vol. 76, No. 4, pp. 1036–1042, (1977), "Effect of Exogeneous Dolichyl Monophosphate on a Developmental Change in Mannosylphosphoryldolichol Biosynthesis", Harford et al.
"Polyisoprenols in Pinus Sylvestris Needles", Hannus et al., Phytochemistry, vol. 13, pp. 2563–2566, (1974).
"Terpenoids of Pinus Strobus Cortex Tissue", Zinkel et al., Phytochemistry, vol. 11, pp. 3387–3389, (1972).
"Synthese Du Squalene Par Couplage Queue a Queue", Biellmann et al; Tetrahedron Letters, No. 42, pp. 3707–3710, (1969).
"The Tissue and Subcellular Districution of [$^3$H]Dolichol in the Rat", Keenan et al; Archives of Biochemistry and Biophysics 179, pp. 634–642, (1977).
"Dolichol: A Naturally–Occurring C$_{100}$ Isoprenoid Alcohol", Burgos et al; Biochem. J. 88, pp. 470–483, (1963).
"Desulfonylation of Aryl Alkyl Sulfones", Trost et al; Tetrahedron Letters, No. 39, pp. 3477–3478 (1976).

Primary Examiner—Alan L. Rotman
Attorney, Agent, or Firm—Burns, Doane, Swecker & Mathis

[57] ABSTRACT

Novel polyprenyl compounds have the general formula:

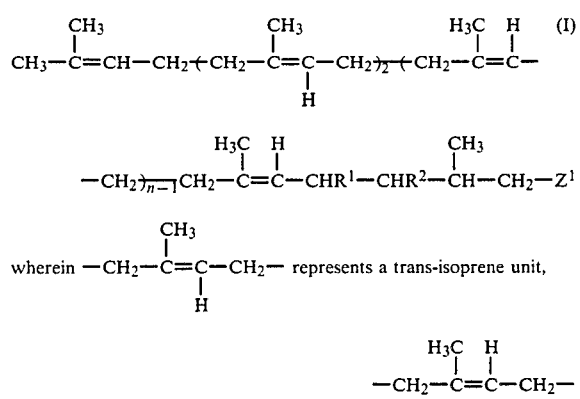

represents a cis-isoprene unit, n is an integer of 11–19, $Z^1$ is —CH$_2$OH or a functional precursor thereof, and either one of $R^1$ and $R^2$ is a hydrogen atom and the other is —S(O)$_m$R$^3$ in which m is an integer of 0 (zero), 1 or 2 and R$^3$ is a phenyl, naphthyl, pyridyl or thiazolinyl group or such group substituted with at least one lower alkyl and/or halogen substituent. The topic novel polyprenyl compounds can be synthesized from derivatives of the polyprenol which is obtainable from leaves of Ginkgo biloba or Cedrus deodara, among others, by extraction, if necessary followed by hydrolytic treatment. The novel polyprenyl compounds can be converted to mammalian dolichols or precursors thereof by reductive elimination of the —S(O)$_m$R$^3$ group.

11 Claims, No Drawings

CERTAIN POLYPRENYL INTERMEDIATES

BACKGROUND OF THE INVENTION

1. Field of the Invention:

The present invention relates to novel polyprenyl compounds and preparation thereof. More particularly, this invention relates to novel polyprenyl compounds useful as intermediates for the synthesis of mammalian dolichols, methods for the preparation of such polyprenyl compounds and the use thereof in the production of mammalian dolichols or precursors thereof.

2. Description of the Prior Art:

Dolichol was first isolated in 1960 from the human kidney and such animal organs as ox kidney, pig kidney, pig heart, pig liver and rat liver by J. F. Pennock et al [see *Nature* (London), 186, 470 (1960)]. Later, it was elucidated that dolichol is a mixture of polyprenol homologs having the general formula:

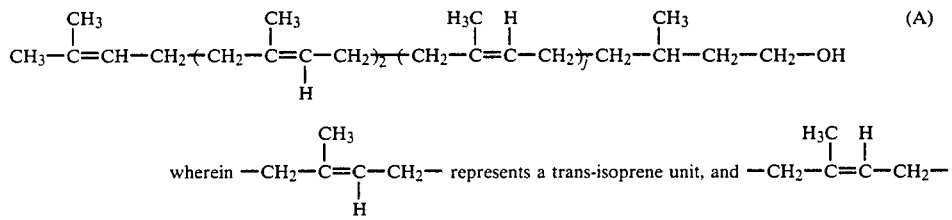

wherein $-CH_2-\underset{H}{\overset{CH_3}{C}}=C-CH_2-$ represents a trans-isoprene unit, and $-CH_2-\overset{H_3C}{C}=\overset{H}{C}-CH_2-$ represents a cis-isoprene unit (the same definitions being consistently applied throughout the present text), and the number j of cis-isoprene units in the above formula is generally distributed between 12 to 18 and the three homologs in which j is 14, 15 and 16 are present in major proportions [R. W. Keenan et al., *Biochemical Journal*, 165, 405 (1977)]. It is also known that dolichol is widely distributed in mammals, and performs a very important function in sustaining the lives of organisms. For example, J. B. Harford et al. demonstrated by in vitro tests using the calf or pig brain white matter that exogenous dolichol enhances incorporation of carbohydrates such as mannose into lipid, and consequently increases the formation of glycoproteins which are important for maintaining the lives of organisms [*Biochemical and Biophysical Research Communications*, 76, 1036 (1977)]. Since the effect of dolichol to incorporate carbohydrates into lipid is remarkable in mature animals as compared with those in the actively growing stage, the action of dolichol has attracted attention for its possible retarding or prevention of aging.

R. W. Keenan et al. state that it is important for organisms which rapidly keep growing, for example, those in the infant stage, to take dolichol extraneously such as to supplement the dolichol produced by biosynthesis within their own body [*Archives of Biochemistry and Biophysics*, 179, 634 (1977)].

Akamatsu et al. determined the quantity of dolichol phosphate in the regenerated liver of a rat and found that the quantity determined is much smaller than that in normal liver and the function of the liver tissues to synthesize glycoproteins is drastically reduced and that the addition of exogenous dolichol phosphate improves the reduced function of glycoprotein synthesis (reported at the 1981 Conference of the Japanese Society of Biochemistry).

Thus, dolichol is a very important substance for living organisms, and it is strongly desired to develop its use as a medicine or an intermediate for the production of medicines, cosmetics, etc.

However, it is not easy to isolate dolichol from mammalian tissues. For example, only about 0.6 g at most of dolichol can be obtained from 10 kg of pig liver through complicated separating procedures [see J. Burgos et al., *Biochemical Journal*, 88, 470 (1963)].

On the other hand, it is extremely difficult by present day techniques of organic synthesis to produce dolichol by a wholly synthetic process, as can be seen in the light of the complex and unique molecular structure thereof.

It to date is known that polyprenols of the general formula

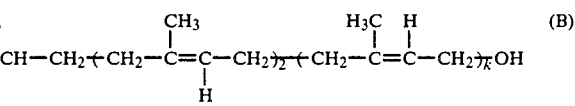

wherein k=4-6, which are called betulaprenols, can be isolated from *Betula verrucola*. However, the betulaprenols to date known contain up to six cis-isoprene units at most, and in order to synthesize dolichol containing homologs having 14, 15 and 16 cis-isoprene units respectively as major components from these betulaprenols, it is necessary to link at least 8 isoprene units while maintaining them in cis-form. This procedure is almost virtually impossible by the present-day organic synthetic techniques.

K. Hannus et al. reported that a polyisoprenyl fraction in an amount of about 1% dry weight was isolated from the needles of *Pinus sylvestris*, and the fraction consisted of polyisoprenyl acetates with 10 to 19 isoprene units predominantly in the cis-configuration [*Phytochemistry*, 13, 2563 (1974)]. However, their report does not explain the details of the trans and cis configurations in said polyprenyl acetates. Furthermore, according to a report of D. F. Zinkel et al., a C$_{90}$ polyprenol containing 18 isoprene units or a homologous series of polyprenols averaging 18 isoprene units is present in *Pinus strobus* needle extracts [cf. *Phytochemistry*, 11, 3387 (1972)]. However, this report does not contain any detailed analysis of the trans and cis configurations in said polyprenol.

Various of the present inventors, together with their colleagues, previously found that extraction of the leaves of *Ginkgo biloba* and *Cedrus deodara* followed by an adequate separation procedure, such as chromatography or fractional dissolution, if necessary following hydrolysis, gives a polyprenyl fraction composed of a mixture of polyprenols and/or acetates thereof which contain 14–22 isoprene units in quite the same trans/cis configurations as in mammalian dolichols and that said polyprenyl fraction is very similar in the distribution of polyprenyl homologs to mammalian dolichols, the only difference being the absence in said fraction of the alpha-terminal saturated isoprene unit and that said polyprenyl fraction, if desired, can be separated relatively easily into the individual constituent polyprenyl homologs (each being homogeneous with respect to the number of isoprene units), and proposed a method of producing dolichols or precursors thereof which comprises reacting such polyprenyl compound or fraction or a reactive derivative thereof with a Grignard reagent or lithium compound derived from a 4-hydroxy-2-methylbutyl halide or a functional precursor thereof (EP 0 054 753 A1 published on June 30, 1982; U.S. patent application Ser. No. 371,487 which is a continuation-in-part of U.S. patent application Ser. No. 324,636, filed Nov. 24, 1981, now abandoned). However, this method is disadvantageous in that the reaction conditions, in particular the kind and amount of the catalyst and the reaction temperature, must be very carefully and strictly selected such as to assure the site selectivity of the coupling reaction and that the solvent must be anhydrous in a strict sense. Furthermore, it is desired that the hydroxyl group of the C$_5$ chain-extender to be used in the above method should be protected.

SUMMARY OF THE INVENTION

Accordingly, a major object of the present invention is the provision of novel polyprenyl compounds useful as intermediates for the production of dolichols, such novel compounds being prepared by a method markedly distinct from that heretofore proposed method outlined above.

Another object of the invention is to provide novel polyprenyl compounds which are useful as intermediates for the synthesis of dolichols and which can be produced without simultaneous formation of regio-isomers.

Yet another object of the invention is to provide a novel method of preparing said novel polyprenyl compounds without formation of position isomers, said method being abundantly satisfactory in operability.

Still another object of the invention is to provide a novel method for preparing dolichols or precursors thereof employing said novel polyprenyl compounds.

Other objects of the invention will become apparent from the description which follows.

Briefly, to accomplish the foregoing objects, the present invention provides polyprenyl compounds [hereinafter sometimes referred to as "polyprenyl compounds (I)"] represented by the general formula:

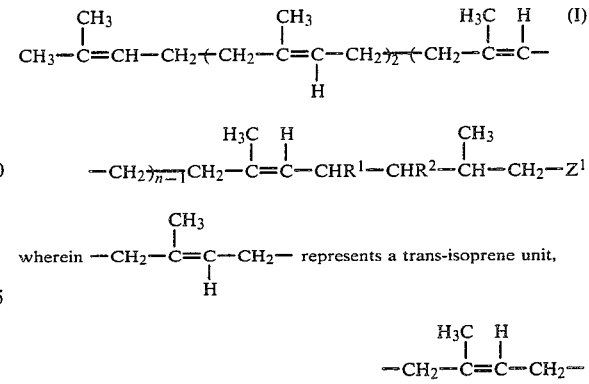

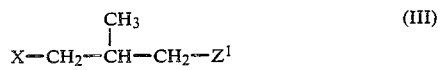

represents a cis-isoprene unit, n is an integer of 11 to 19, $Z^1$ is —CH$_2$OH or a functional group precursor thereof and either one of $R^1$ and $R^2$ is a hydrogen atom and the other is —S(O)$_m$R$^3$ in which m is an integer of 0 (zero), 1 or 2 and $R^3$ is a phenyl, naphthyl, pyridyl or thiazolinyl group which may have one or more substituents selected from lower alkyl groups and halogen atoms.

It has now been found that said polyprenyl compounds (I) can readily be prepared, without concomitant formation of regio-isomers, by reacting a compound of the general formula:

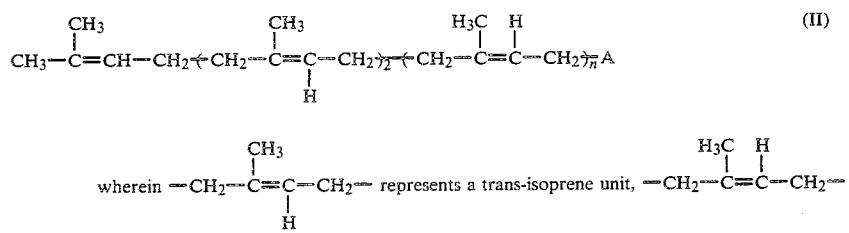

represents a cis-isoprene unit, n is an integer of 11 to 19 and A is a halogen atom or an —S(O)$_m$R$^3$ group in which m is an integer of 0 (zero), 1 or 2 and $R^3$ is a phenyl, naphthyl, pyridyl or thiazolinyl group which may have one or more substituents selected from lower alkyl groups and halogen atoms, with a compound of the general formula $$\underset{\underset{\text{X—CH}_2\text{—CH—CH}_2\text{—Z}^1}{|}}{\text{CH}_3} \qquad (III)$$

wherein X is an —S(O)$_m$R$^3$ group when A in general formula (II) is a halogen atom and X is a halogen atom when said A is an —S(O)$_m$R$^3$ group, and $Z^1$ is —CH$_2$OH or a functional group precursor thereof, m and $R^3$ being as defined above, with the aid of an anionizing agent. Removal of the —S(O)$_m$R$^3$ group of the polyprenyl compounds (I) by a reductive elimination reaction, if necessary following or followed by conversion of the functional precursor group $Z^1$ to —CH$_2$OH when $Z^1$ is such group, facilely provides polyprenyl compounds, namely dolichols or precursors thereof, of the general formula:

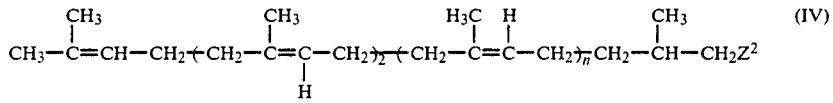

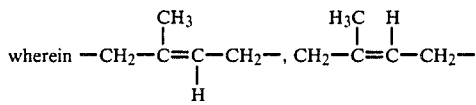

and n are as defined above and $Z^2$ is $-CH_2OH$ or the same functional precursor group as $Z^1$ in general formula (I) when $Z^1$ is such group.

The condensation reaction between a compound of general formula (II) and a compound of general formula (III), as mentioned above, gives a compound of general formula (I) with very high site specificity. The configuration of the polyprenyl group in the starting material and the conformation of the methyl group in the compound of general formula (III) are retained without substantial alteration throughout the above reaction. Therefore, the dolichols prepared by the method of the invention using the compounds of the invention are useful as valuable physiologically active substances in the fields mentioned above, namely in the fields of medicines and cosmetics, among others, just as the dolichols isolated from mammalian tissues.

DETAILED DESCRIPTION OF THE INVENTION

More particularly according to this invention, in general formula (I), either one of $R^1$ and $R^2$ is an $-S(O)_mR^3$ group, and either one of A in general formula (II) and X in general formula (III) is also an $-S(O)_mR^3$ group. The $R^3$ moiety in said $-S(O)_mR^3$ group preferably is a phenyl group or a lower alkyl- or halogen-substituted phenyl group, most preferably a phenyl, tolyl or monochlorophenyl group. The value of m is preferably 2. The halogen atom represented by A in general formula (II) or by X in general formula (III) is, for example, a chlorine, bromine or iodine atom, preferably a chlorine or bromine atom. $Z^1$ in general formulas (I) and (III) and $Z^2$ in general formula (IV) each is a $-CH_2OH$ group or a precursor group thereof. The functional precursor group includes hydroxymethyl and aldehyde groups protected by protective groups which can be easily split off by such treatment as hydrolysis or hydrogenolysis. The aldehyde group, after removal of the protective group, can be converted to a hydroxymethyl group by subjecting it to mild reducing conditions, for example reduction with a complex metal hydride compound such as sodium borohydride, lithium borohydride, lithium aluminum hydride or sodium aluminum hydride.

Specific examples of such functional precursor groups are as follows:

(1) Groups of the formula $-CH_2O-R^4$ represents a lower alkyl group, an aralkyl group having 7 to 11 carbon atoms, an aliphatic or alicyclic ether residue having 1 to 8 carbon atoms, or a silyl group of the formula $-Si(R_{51})(R_{52})(R_{53})$ in which each of $R_{51}$, $R_{52}$ and $R_{53}$ represents a lower alkyl group, a phenyl group, a tolyl group or a xylyl group.

Examples are as follows:
$-CH_2OCH_3$, $-CH_2OC_2H_5$, $-CH_2OC_3H_7$, $-CH_2OC_4H_9$, $-CH_2OC_5H_{11}$, $-CH_2OCH_2OCH_3$, $-CH_2OCH_2OC_2H_5$, $-CH_2OC_3H_6OCH_3$, $-CH_2OC_3H_6OC_2H_5$, $-CH_2OC_2H_4OC_2H_4OCH_3$, $-CH_2OCH_2OC_2H_4OCH_3$,

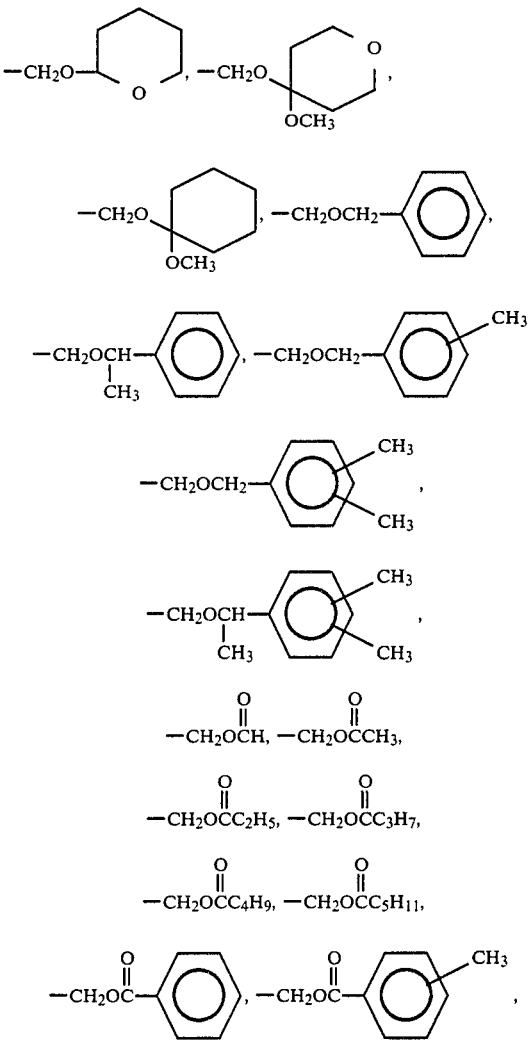

$-CH_2OSi(CH_3)_3$, $-CH_2OSi(C_2H_5)(C_3H_7)CH_3$, $-CH_2OSi(CH_3)_2C_4H_9\text{-}t$, $-CH_2OSi(t\text{-}C_4H_9)(C_6H_5)_2$, $-CH_2OSi(C_6H_5)_3$ (2) Groups of the formula

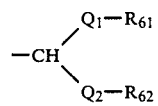

wherein $Q_1$ and $Q_2$ each represents an oxygen or sulfur atom, and $R_{61}$ and $R_{62}$ each represents a lower alkyl group, or when taken together, represent a lower alkylene group.

Examples are as follows:

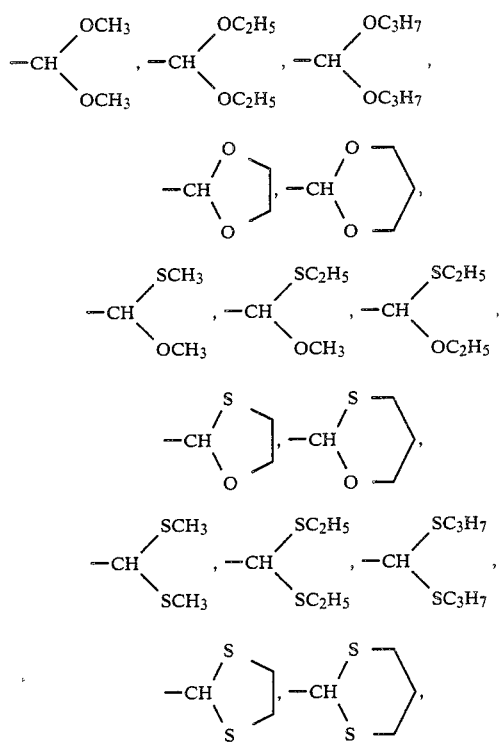

The functional group precursors of —CH2OH represented by $Z^1$ and $Z^2$ may be other than those mentioned above. However, as $Z^1$ in the compound of general formula (III), a free hydroxymethyl group is preferred to a protected hydroxymethyl group especially for reasons that the free hydroxymethyl group does not affect the condensation reaction between the compound of general formula (III) and the compound of general formula (II) and that the resulting polyprenyl compounds of general formula (I) can be converted to dolichols in one step by elimination of the —S(O)$_m$R$^3$ group.

The compounds of general formula (II) can easily be prepared from polyprenols of the general formula:

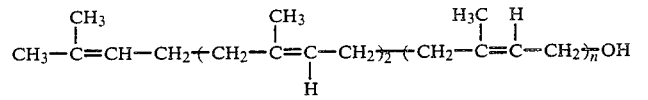

(V)

wherein n is as defined above, which can be obtained from *Ginkgo biloba* or *Cedrus deodara* leaf extracts either directly or via hydrolysis.

The polyprenyl halides of general formula (II) in which A is a halogen atom can be prepared by halogenating a polyprenol or polyprenol mixture represented by general formula (V) with a halogenating agent such as a phosphorus trihalide or a thionyl halide. This halogenation reaction can be carried out in an appropriate solvent, such as hexane or diethyl ether, in the presence or absence of a base such as triethylamine or pyridine, at a temperature of about −20° C. to +50° C., with dropwise addition of PCl$_3$, SOCl$_2$, PBr$_3$, SOBr$_2$ or the like.

The polyprenyl sulfides of general formula (II) in which A is —SR$^3$ can be synthesized by reacting the above-mentioned polyprenyl halides with the corresponding mercaptan (R$^3$SH). This reaction is typically carried out in a solvent such as dimethylformamide or tetrahydrofuran, in the presence of a base such as sodium hydride, sodium hydroxide, potassium hydroxide or sodium tert-butoxide, at room temperature. The polyprenyl sulfoxides of general formula (II) in which A is —SOR$^3$ can be produced by treating the above-mentioned polyprenyl sulfides with a slightly excessive amount of an oxidizing agent such as sodium periodate or hydrogen peroxide. This oxidation reaction is typically conducted in a medium such as aqueous methanol or aqueous acetone, at room temperature or in the vicinity thereof. The polyprenyl sulfones of general formula (II) in which A is —SO$_2$R$^3$ can be prepared by reacting the above-mentioned polyprenyl halides with an alkali metal salt of the corresponding organic sulfuric acid R$^3$SO$_2$M in which M is an alkali metal, preferably Na) in a solvent such as dimethylformamide or tetrahydrofuran, at a temperature of from room temperature to about 70° C.

Most of the compounds of formula (III) are known, and those which are novel can be easily prepared in accordance with the methods for producing the known compounds.

The reaction of the compound of general formula (II) with the compound of general formula (III) is typically carried out in a solvent which is preferably inert to the reaction. Solvents useful in most cases are ether-type solvents, typically diethyl ether, diisopropyl ether, tetrahydrofuran, dimethoxyethane and diethylene glycol dimethyl ether. It is also possible to use a mixed solvent compound of such an ether-type solvent and an inert polar solvent such as hexamethylphosphoramide. It is preferable that the solvent to be used in this reaction is dried to an anhydrous state, although the extent of dehydration need not be so strict as in the case of the reaction using an organomagnesium compound. The above reaction is carried out with the aid of an anionizing agent selected from among strong bases, typically sodium hydride, potassium hydride, methyllithium, n-butyllithium and tertbutyllithium. Generally, each mole of the compound of general formula (II) in which A is —S(O)$_m$R$^3$ or the compound of general formula (III) in which X is —S(O)$_m$R$^3$ is subjected to the action of 0.8 to 2.0 moles, preferably 1.0 to 1.2 moles, [1.6 to 4.0 moles, preferably 2.0 to 2.4 moles, per mole of compound (III) where $Z^1$ is —CH$_2$OH], of the anionizing agent, in an inert solvent such as mentioned above, at a temperature of about −80° C. to +80° C., preferably about −30° C. to +5° C., for formation of a carbanion, followed by addition of about 0.8 to 3.0 moles, preferably 1.0 to 1.5 moles of the compound of general formula (III) in which X is a halogen atom or the compound of general formula (II) in which A is a halogen atom per mole of the above starting compound having the —S(O)$_m$R$^3$ group at a temperature of about −80° C. to +80° C., preferably −30° C. to +5° C., for effecting the desired reaction. The thus-obtained novel polyprenyl compounds of general formula (I) contain two asymmetric centers, one being the carbon atom to which —S(O)$_m$R$^3$ is bonded and the other being the carbon atom located between said carbon atom and Z$^1$ with a methyl group being bonded thereto, and accordingly the diastereomer ratio in the product may vary depending on the reaction conditions, among others. However, the present invention is not to be considered as being limited with regard to said ratio or to the presence or absence of an optical activity, either.

The polyprenyl compounds (I), when subjected to reductive elimination of the —S(O)$_m$R$^3$ group, if necessary followed by conversion of the functional group precursor of a hydroxymethyl group to a hydroxymethyl group when Z$^1$ is such precursor group, provide the compounds of general formula (IV). Alternatively, the reductive —S(O)$_m$R$^3$ elimination may be carried out following the conversion of the functional precursor group of a hydroxymerthyl group in the polyprenyl compounds (I) to a hydroxymethyl group or, when the functional precursor group is a protected —CHO group, followed the conversion of said group to a free —CHO group or a hydroxymethyl group. Especially when Z$^1$ in general formula (I) is a sulfur atom-containing group, it is desirable to conduct the reductive —S(O)$_m$R$^3$ elimination reaction after conversion of said sulfur atom-containing group to a sulfur atom-free group, for example a hydroxymethyl group or a —CHO group.

The reductive —S(O)$_m$R$^3$ elimination from the polyprenyl compound (I) or an unblocked protected derivative thereof can be effected by the methods known to be effective for achieving similar objects with regard to known organic sulfides, sulfoxides or sulfones, using for instance Na-Hg [cf. B. M. Trost et al., *Tetrahedron Letters*, 3477 (1976)], Al-Hg [cf. E. J. Corey et al., *J. Am. Chem. Soc.*, 86, 1639 (1964); K. Sisido et al., *J. Am. Chem. Soc.*, 81, 5817 (1959)], alkali metal-amine [cf. E. M. Kaiser et al., *Synthesis*, 391 (1972); J. F. Biellmann et al., *Tetrahedron Letters*, 3707 (1969); H. O. Huisman, *Pure and Applied Chemistry*, 49, 1307 (1977)] or Raney Ni [cf. K. Hirai et al., *Tetrahedron Letters*, 4359 (1971)]. Among these, the method using an alkali metal-amine system is particularly preferred. In this method, suitable examples of the alkali metal are lithium, sodium and potassium, among which lithium is especially preferred. The alkali metal is preferably used in an amount of about 5 to 50 times the stoichiometric amount. The amine is, for example, a mono- or di-lower alkylamine such as methylamine, ethylamine, propylamine, dimethylamine or diethylamine, or ammonia, and methylamine, ethylamine and ammonia are preferred, among others. This reaction is desirably carried out in an inert gas atmosphere such as nitrogen or argon, at a temperature of about −80° C. to +10° C., preferably about −50° C. to 0° C.

Removal of the protective group from the compound of formula (I) or (IV) can be effected by hydrolysis or hydrogenolysis in accordance with methods known per se.

For example, when Z$^1$ or Z$^2$ represents —CH$_2$—O—R$^4$ and R$^4$ represents a lower alkyl group, the compound of formula (I) or (IV) may be unblocked by treating it with iodotrimethylsilane in a solvent such as tetrahydrofuran, chloroform or methylene chloride at room temperature. When R$^4$ in the above group —CH$_2$—O—R$^4$ is an aralkyl group, the compound of general formula (I) or (IV) can be unblocked by adding a solution thereof in tetrahydrofuran dropwise to a solution of lithium in ethylamine and, after completion of the reaction, decomposing the excess lithium with a saturated aqueous ammonium chloride, for example. In that case, the —S(O)$_m$R$^3$ group can be eliminated simultaneously. When R$^4$ in the above formula represents an ether residue, the protective group may be removed by dissolving the compound of formula (I) or (IV), for example, in a mixed solvent of hexane-ethanol (about 1:1), adding pyridinium p-toluenesulfonate (preferably in an amount of about 0.1 to 0.2 equivalent) to the solution, heating the mixture at about 50° to 60° C. for several hours, and after the reaction, neutralizing the reaction mixture with sodium carbonate or the like. When R$^4$ in the above formula represents a silyl group, the unblocking may be carried out by adding tetra-n-butylammonium fluoride (preferably in an amount of about 2 equivalents) to a tetrahydrofuran solution of the compound of formula (I) or (IV), and stirring the mixture overnight at room temperature.

On the other hand, when Z$^1$ or Z$^2$ represents the above-mentioned formula

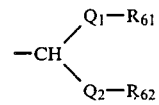

in which neither of Q$_1$ and Q$_2$ is a sulfur atom, Z$^1$ or Z$^2$ can be converted to an aldehyde group (—CHO) by treating the compound of general formula (I) or (IV) in a solvent such as tetrahydrofuran or isopropyl alcohol with diluted hydrochloric acid (preferably having a concentration of about 10%), for example. When at least one of Q$_1$ and Q$_2$ is a sulfur atom, it is preferable to unblock the compound of general formula (I), i.e. to convert Z$^1$ to —CHO, prior to the reductive —S(O)$_m$R$^3$ elimination, and for this purpose, there may be used, for example, a method comprising adding HgCl$_2$ and CdCO$_3$ in at least equivalent amounts, together with a small amount of water, to an acetone solution of the compound of general formula (I) and allowing the reaction to proceed at room temperature for several hours.

The aldehyde group thus unblocked can be converted to a hydroxymethyl group (—CH$_2$OH) by reduction under mild reducing conditions, for example with a complex metal hydride such as sodium borohydride, lithium borohydride, lithium aluminum hydride or sodium aluminum hydride. The reduction can be carried out by methods known per se. For example, when sodium borohydride is used as the reducing agent, the reaction is desirably carried out at about 0° C. to room temperature in a solvent such as ethanol, tetrahydrofuran or diethyl ether. When lithium borohydride, lithium aluminum hydride or sodium aluminum hydride is used as the reducing agent, the reducing reaction is advantageously carried out at about −30° C. to room temperature in an anhydrous solvent such as anhydrous diethyl ether or tetrahydrofuran.

After the reduction, the reaction mixture is treated with water, alcohol, ethyl acetate or the like to decompose the excess of the reducing agent, and the product separated and purified in a usual manner to give the desired alcohol [the compound of formula (I) or (IV) in which Z$^1$ or Z$^2$ is a hydroxymethyl group] in high yields. The thus-obtained compound of general formula (I) in which Z$^1$ is a hydroxymethyl group is converted to the compound of general formula (IV) in which Z$^2$ is a hydroxymethyl group by subjecting the compound (I) to reductive $-S(O)_mR^3$ elimination in the manner outlined above.

The method of the present invention is not only applicable to individual single polyprenyl compounds each homogeneous with regard to the value of n, but also equally applicable to polyprenyl compositions displaying various distribution patterns with regard to the value of n (i.e., mixtures of polyprenyl compounds).

The mammalian dolichols synthesized in the manner mentioned above are, also as mentioned above, useful as physiologically active agents valuable in the fields of medicines and cosmetics, among others.

In order to further illustrate the present invention and the advantages thereof, the following specific examples and Reference Examples are given, it being understood that same are intended only as illustrative and in nowise limitative.

In the Examples and Reference Examples, the IR analysis was performed by the liquid film method, and the NMR analysis was carried out with TMS (tetramethylsilane) as an internal standard. The FD-MASS analysis values are the values corrected on the $^1H$, $^{12}C$, $^{14}N$, $^{16}O$, $^{28}Si$, $^{32}S$, $^{35}Cl$ and $^{79}Br$ basis.

EXAMPLE 1

4-Phenylsulfonyl-3-methyl-1-butanol (1.14 g) synthesized in accordance with Reference Example 11 (to follow) was dissolved in a mixture of 30 ml of anhydrous tetrahydrofuran and 3 ml of anhydrous hexamethylphosphoramide, the solution cooled to about −10° C. to 0° C., 6.56 ml of a 1.6M solution of n-butyllithium in hexane next added in a nitrogen atmosphere, the mixture stirred for 15 minutes, and then a solution of 6.52 g of a polyprenyl bromide of the general formula (II) in which n=15 and A=Br (synthesized in accordance with Reference Example 2 to follow) in 5 ml of anhydrous tetrahydrofuran was added dropwise. After the dropping, the mixture was stirred at the same temperature for one hour and then at room temperature (about 20° C.) overnight. The reaction mixture was then poured into 200 ml of water, neutralized with diluted hydrochloric acid and extracted with methylene chloride. The methylene chloride layer was washed with water and dried over anhydrous magnesium sulfate, and the solvent was then distilled off under reduced pressure. A pale yellow liquid was obtained. This liquid was purified by silica gel column chromatography (developing solvent: methylene chloride-tetrahydrofuran) to give 5.40 g of a slightly yellow liquid. The analytical results reported below demonstrated that the product was 4-phenylsulfonyl-4-polyprenyl-3-methyl-1-butanol [Compound (1); in general formula (I), n=15, $R^1$=H, $R^2$=$-SO_2C_6H_5$, $Z^1$=$-CH_2OH$].

FD-MASS: m/e=1452

IR(cm$^{-1}$): 3525, 3040, 2975, 2930, 2850, 1670, 1580, 1450, 1380, 1310, 1150, 1090, 840, 725, 690

$^1$H-NMR($\delta_{ppm}^{CDCl_3}$):

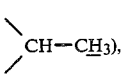
1.02 and 1.06(each d, 3H, CH—CH$_3$), 1.52(s, 9H, ), 1.64(s, 48H, CH$_3$ ), 3.00(t, 1H, CH—SO$_2$), 3.46–3.80(m, 2H, —CH$_2$O), 4.80(t, 1H, CH—), 5.07(bs, 17H, CH—), 7.42–7.94(m, 5H, SO$_2$—C$_6$H$_5$)

The analysis of $^1$H-NMR spectra was performed for the above characteristic signals because of the above substance being a macromolecule.

This compound (1) (5.30 g) was dissolved in 100 ml of anhydrous ethylamine, and the solution was cooled to −20° C. and, following addition of 0.50 g of metallic lithium, stirred in a nitrogen atmosphere. After the reaction mixture turned blue, stirring was continued for 15 minutes. Then, 2 ml of isoprene and 2 ml of methanol were added followed by 2 g of ammonium chloride for decomposing the excess lithium. The system turned white, when the mixture was poured into 200 ml of water. Extraction with hexane, washing of the hexane extract with water followed by drying over anhydrous magnesium sulfate, removal of the hexane under reduced pressure and purification of the residue by silica gel column chromatography (developing solvent: methylene chloride-ethyl acetate) gave 3.51 g of a colorless, viscous liquid. The analytical results reported below demonstrated that the above product was a compound of general formula (IV) in which n=15 and $Z^2$=—CH$_2$OH.

FD-MASS: m/e=1312

IR(cm$^{-1}$): 3320, 2920, 2850, 1440, 1376, 1060, 830

$^{13}$C-NMR(ppm/intensity): 135.365/430, 135.229/3567, 135.005/349, 134.937/290, 131.210/213, 125.071/5242, 124.993/499, 124.448/505, 124.282/463, 124.214/445, 61.241/551, 40.029/541, 39.757/683, 37.548/582, 32.245/5500, 32.021/456, 29.316/528, 26.825/492, 26.699/548, 26.436/5166, 25.677/542, 25.308/567, 23.430/6330, 19.557/548, 17.679/353, 16.006/640

$^1$H-NMR(ppm, shape of signal, proton ratio): 0.91(d, 3H), 1.10–1.80(m, 5H), 1.60(s, 9H), 1.68(s, 48H), 2.03(b, 70H), 3.66(m, 2H), 5.10(b, 18H).

EXAMPLES 2-7

Using the compounds of general formula (II) and the compounds of general formula (III) respectively specified in Table 1 in the amounts also specified in said table, the corresponding compounds of general formula (I) were synthesized by the same procedure as described in Example 1. The compounds of general formula (I) thus obtained were subjected to desulfonylation in the same manner as in Example 1 to give a compound of general formula (IV) in which n=15 and $Z^2$=—CH$_2$OH and the physical characteristics of which were in agreement with those of the final product in Example 1. The physical characteristics of the compounds of general formula (I) synthesized herein were as follows:

4-(Meta-tolylsulfonyl)-4-polyprenyl-3-methyl-1-butanol [Compound (2)]:

FD-MASS: m/e=1466

IR(cm$^{-1}$): 3525, 1670, 1600, 1140

$^1$H-NMR($\delta_{ppm}^{CDCl_3}$):

1.06(d, 3H, 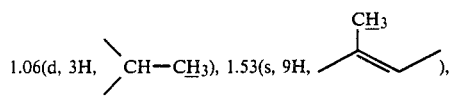), 1.53(s, 9H, 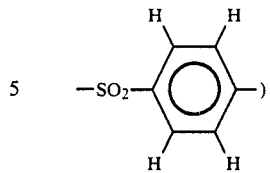), 1.61(s, 48H, 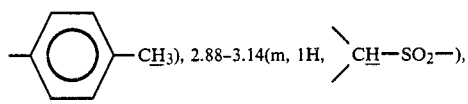), 2.38(s, 3H, -SO₂-⬡-C<u>H</u>₃), 2.88-3.14(m, 1H, 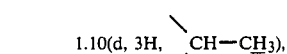), 3.40-3.86(m, 2H, -C<u>H</u>₂O-), 4.85(t, 1H, 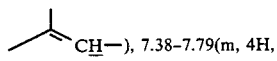), 5.12(bs, 17H,

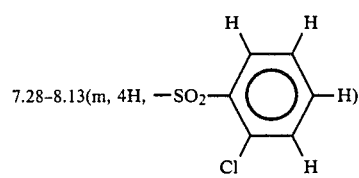), 7.38-7.79(m, 4H,

-SO₂-⬡)

4-(Para-tolylsulfonyl)-4-polyprenyl-3-methyl-1-butanol [Compound (3)]:

FD-MASS: m/e=1466
IR(cm⁻¹): 3525, 1670, 1595, 1140
¹H-NMR($\delta_{ppm}^{CDCl_3}$):

1.06(d, 3H, 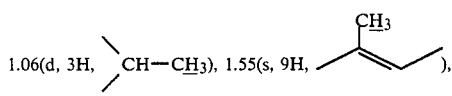), 1.55(s, 9H, CH₃ ), 1.62(s, 48H, C<u>H</u>₃ ), 2.40(s, 3H, -SO₂-⬡-C<u>H</u>₃), 2.87-3.11(m, 1H,

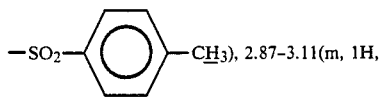), 3.40-3.87(m, 2H, -C<u>H</u>₂O-), 4.85(t, 1H, ⬇C<u>H</u>-), 5.12(bs, 17H, ⬇C<u>H</u>-), 7.28 and 7.72(each d, 4H, -continued

-SO₂-⬡)

4-(Ortho-chlorophenylsulfonyl)-4-polyprenyl-3-methyl-1-butanol [Compound (4)]:

FD-MASS: m/e=1486
IR(cm⁻¹): 3525, 1670, 1580, 1150
¹H-NMR($\delta_{ppm}^{CDCl_3}$):

1.10(d, 3H, CH-CH₃), 3.40-3.87(m, 3H, -C<u>H</u>₂O-, 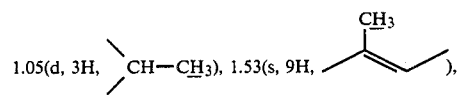), 4.78(t, 1H, ⬇C<u>H</u>-), 5.08(bs, 17H, ⬇C<u>H</u>-), 7.28-8.13(m, 4H, -SO₂-⬡-Cl)

4-(Para-chlorophenylsulfonyl)-4-polyprenyl-3-methyl-1-butanol [Compound (5)]:

FD-MASS: m/e=1486
IR(cm⁻¹): 3525, 1670, 1580, 1475, 1145
¹H-NMR($\delta_{ppm}^{CDCl_3}$):

1.05(d, 3H, CH-CH₃), 1.53(s, 9H, CH₃ ), 1.62(s, 48H, C<u>H</u>₃ ), 2.90-3.14(m, 1H,

C<u>H</u>-SO₂-), 3.38-3.86(m, 2H, -C<u>H</u>₂O-), 4.80(t, 1H, ⬇C<u>H</u>-), 5.07(bs, 17H, ⬇C<u>H</u>-), 7.44 and 7.80(each d, 4H, 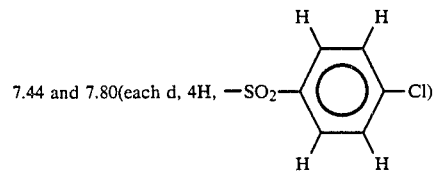)

4-(Beta-naphthylsulfonyl)-4-polyprenyl-3-methyl-1-butanol [Compound (6)]:
FD-MASS: m/e=1502
IR(cm$^{-1}$): 3525, 1670, 1620, 1590, 1300, 1140, 1120
$^1$H-NMR($\delta_{ppm}^{CDCl_3}$):
1.00(d, 3H, \>CH—C<u>H</u>$_3$), 1.52(s, 9H, 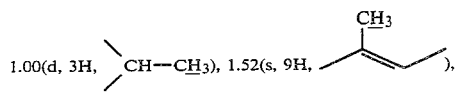),
1.62(s, 48H, C<u>H</u>$_3$ ), 2.80-3.08(m, 1H,
\>C<u>H</u>—SO$_2$—), 3.40-3.91(m, 2H, —C<u>H</u>$_2$O—),
4.81(t, 1H, \>CH—), 5.09(bs, 17H, \>C<u>H</u>=),
7.31-8.55(m, 7H, —SO$_2$—C$_{10}$<u>H</u>$_7$)

TABLE 1

| Ex. No. | Compound of general formula (II) n | Compound of general formula (II) A | Compound of general formula (II) Amount (g) | Compound of general formula (III) X | Compound of general formula (III) Z¹ | Compound of general formula (III) Amount (g) | Compd. No. | n | R¹ | R² | Z¹ | Yield (g) | Amount* (g) | Yield of Compd. (IV) (g) |
|---|---|---|---|---|---|---|---|---|---|---|---|---|---|---|
| 1 | 15 | Br | 6.52 |  | —CH₂OH | 1.14 | (1) | 15 | H |  | —CH₂OH | 5.40 | 5.30 | 3.51 |
| 2 | " | " | " |  | " | 1.21 | (2) | " | " |  | " | 5.42 | 5.32 | 3.68 |
| 3 | " | " | " |  | " | " | (3) | " | " | 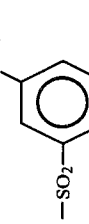 | " | 6.08 | 6.00 | 4.04 |
| 4 | " | " | " |  | " | 1.31 | (4) | " | " | 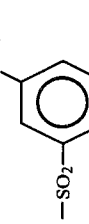 | " | 5.28 | 5.18 | 3.30 |
| 5 | " | " | " |  | " | " | (5) | " | " |  | " | 4.46 | 4.36 | 3.05 |
| 6 | " | " | " |  | " | 1.39 | (6) | " | " |  | " | 3.98 | 3.90 | 2.53 |
| 7 | " | Cl | 6.30 |  | " | 1.14 | (1) | " | " |  | " | 5.23 | 5.13 | 3.38 |

*Amount used for the production of compound of general formula (IV)

EXAMPLE 8

Following the procedure of Example 1, except that 1.62 g of 4-phenylsulfonyl-3-methylbutyl acetate was used in place of 4-phenylsulfonyl-3-methyl-1-butanol, there were obtained 5.98 g of 4-phenylsulfonyl-4-polyprenyl-3-methylbutyl acetate [Compound (7); in general formula (I), n=15, $R^1$=H, $R^2$=—$SO_2C_6H_5$, $Z^1$=—$CH_2OCOCH_3$], which has the following physical characteristics:

FD-MASS: m/e=1494
IR($cm^{-1}$): 1730, 1670, 1580, 1140
$^1$H-NMR($\delta_{ppm}^{CDCl_3}$):

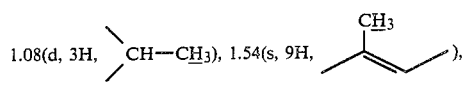

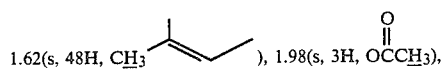

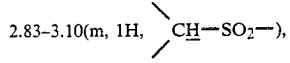

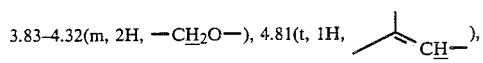

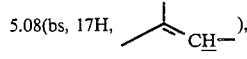

7.35–7.98(m, 5H, —$SO_2$—$C_6H_5$)

This compound (7) (5.88 g) was desulfonylated in the same manner as in Example 1 (the amount of metallic lithium was 0.56 g). The crude product obtained (residue after removal of hexane by distillation under reduced pressure) was dissolved in 150 ml of ethanol, 30 ml of 10% aqueous sodium hydroxide added, and the mixture stirred at room temperature for 5 hours. Then, most of the ethanol was distilled off under reduced pressure, the residue poured into 200 ml of water and extracted with hexane, the hexane layer was washed well with water and then dried over anhydrous magnesium sulfate, the hexane distilled off under reduced pressure, and the residue purified by silica gel column chromatography (developing solvent: methylene chloride-ethyl acetate). There were obtained 3.41 g of a colorless, viscous oil. The FD-MASS, IR, $^{13}$C-NMR and $^1$H-NMR spectra of this product were in agreement with those of the final product in Example 1 and thus it was confirmed that this substance was the compound of general formula (IV) in which n=15 and $Z^2$=—$CH_2OH$.

EXAMPLE 9

The procedure of Example 1 was repeated, except that 1.87 g of 4-phenylsulfonyl-3-methylbutyl tetrahydropyranyl ether was used in place of 4-phenylsulfonyl-3-methyl-1-butanol and there were obtained 5.84 g of 4-phenylsulfonyl-4-polyprenyl-3-methylbutyl tetrahydropyranyl ether [Compound (8); in general formula (I), n=15, $R^1$=H, $R^2$=—$SO_2C_6H_5$,

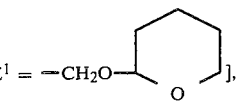

which had the following physical characteristics:
FD-MASS: m/e=1536
IR($cm^{-1}$): 1670, 1590, 1145, 1075, 1035
$^1$H-NMR($\delta_{ppm}^{CDCl_3}$):

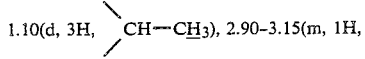

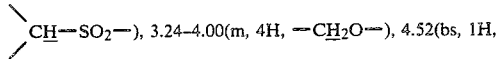

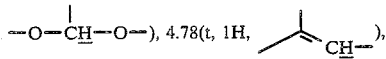

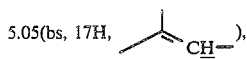

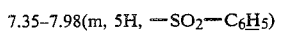

7.35–7.98(m, 5H, —$SO_2$—$C_6H_5$)

This compound (8) (5.79 g) was desulfonylated in the same manner as in Example 1 (0.56 g of metallic lithium was used). The crude product obtained (residue after removal of hexane by distillation under reduced pressure) was dissolved in 150 ml of ethanol, 30 ml of 1N HCl added, and the mixture stirred at room temperature for 3 hours. Then, most of the ethanol was distilled off under reduced pressure, the residue poured into 200 ml of water and extracted with hexane, the hexane layer washed well with water and dried over anhydrous magnesium sulfate, the hexane then distilled off, and the residue purified by silica gel column chromatography (developing solvent: methylene chloride-ethyl acetate). There were obtained 3.40 g of a compound of general formula (IV) in which n=15 and $Z^2$=—$CH_2OH$. The physical characteristics of the compound were in agreement with those of the final product in Example 1.

EXAMPLE 10

Following the procedure of Example 1, except that 1.97 g of 4-phenylsulfonyl-3-methylbutyl 1-(n-butoxy)ethyl ether was used in place of 4-phenylsulfonyl-3-methyl-1-butanol, there were obtained 5.28 g of 4-phenylsulfonyl-4-polyprenyl-3-methylbutyl 1-butoxyethyl ether [Compound (9); in general formula (I), n=15, $R^1$=H, $R^2$=—$SO_2C_6H_5$, $Z^1$=—$CH_2OCH(CH_3)O(CH_2)_3$—$CH_3$], which has the following physical characteristics:

FD-MASS: m/e=1552
IR($cm^{-1}$): 1670, 1590, 1450, 1300, 1150, 1090
$^1$H-NMR($\delta_{ppm}^{CDCl_3}$):

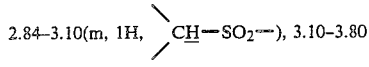

(m, 4H, —C$\underline{H}$$_2$—O—C$\underline{H}$—OC$\underline{H}$$_2$—), 4.46-4.70(m, 1H, —O—C$\underline{H}$—O—), 4.85(t, 1H, $\diagup\hspace{-0.5em}\diagdown$$_{C\underline{H}-}$), 5.09(bs, 17H, $\diagup\hspace{-0.5em}\diagdown$$_{C\underline{H}-}$), 7.32-7.98(m, 5H, —SO$_2$—C$_6$$\underline{H}$$_5$)

5.20 g of this compound (9) were desulfonylated in the same manner as in Example 1, followed by protective group removal in the same manner as in Example 9. There was obtained 3.18 g of the compound of general formula (IV) in which n=15 and Z$^2$=—CH$_2$OH.

EXAMPLE 11

Following the procedure of Example 1 except that 1.80 g of 4-phenylsulfonyl-3-methylbutyl trimethylsilyl ether was used in place of 4-phenylsulfonyl-3-methyl-1-butanol, there were obtained 5.33 g of 4-phenylsulfonyl-4-polyprenyl-3-methylbutyl trimethylsilyl ether [Compound (10); in general formula (I), n=15, R$^1$=H, R$^2$=—SO$_2$C$_6$H$_5$, Z$^1$=—CH$_2$OSi—(CH$_3$)$_3$], which has the following physical characteristics:

FD-MASS: m/e=1524
IR(cm$^{-1}$): 1670, 1590, 1310, 1250, 1150, 1090, 845
$^1$H-NMR($\delta_{ppm}$$^{CDCl3}$):

1.03(d, 3H, CH—C$\underline{H}$$_3$), 1.50(s, 9H, $\diagup\hspace{-0.5em}\diagdown$$^{CH_3}$), 1.59(s, 48H, C$\underline{H}$$_3$$\diagup\hspace{-0.5em}\diagdown$), 2.80-3.08(m, 1H, C$\underline{H}$—SO$_2$—), 3.34-3.74(m, 2H, —C$\underline{H}$$_2$O—), 4.81(t, 1H, $\diagup\hspace{-0.5em}\diagdown$$_{C\underline{H}-}$), 5.07(bs, 17H, $\diagup\hspace{-0.5em}\diagdown$$_{C\underline{H}-}$), 7.21-7.98(m, 5H, —SO$_2$—C$_6$$\underline{H}$$_5$)

5.28 g of this compound (10) were dissolved in 150 ml of ethanol, 20 ml of 1N HCl added, and the mixture stirred at room temperature for 5 hours. Then, most of the ethanol was distilled off under reduced pressure, the residue poured into 200 ml of water and extracted with methylene chloride, the methylene chloride layer washed with water and dried over anhydrous magnesium sulfate, and the solvent distilled off under reduced pressure. The IR spectrum of the thus-obtained slightly yellow liquid was in agreement with that of Compound (1) synthesized in Example 1. The above slightly yellow liquid was subjected to desulfonylation by the procedure of Example 1 to give 2.98 g of the compound of general formula (IV) in which n=15 and Z$^2$=—CH$_2$OH. The FD-MASS, IR, $^{13}$C-NMR and $^1$H-NMR spectra were in agreement with those of the final product obtained in Example 1.

EXAMPLE 12

Following the procedure of Example 1, except that 1.91 g of 4-phenylsulfonyl-3-methylbutyl benzyl ether was used in place of 4-phenylsulfonyl-3-methyl-1-butanol, there were obtained 4.24 g of 4-phenylsulfonyl-4-polyprenyl-3-methylbutyl benzyl ether [Compound (11); in general formula (I), n=15, R$^1$=H, R$^2$=—SO$_2$C$_6$H$_5$, Z$^1$=—CH$_2$OCH$_2$C$_6$H$_5$], which had the following physical characteristics:

FD-MASS: m/e=1542
IR(cm$^{-1}$): 1660, 1580, 1500, 1300, 1140, 1100, 700
$^1$H-NMR($\delta_{ppm}$$^{CDCl3}$):

1.03 & 1.06(each d, 3H, CH—C$\underline{H}$$_3$), 4.35 & 4.42(each s, 2H, —O—C$\underline{H}$$_2$—C$_6$H$_5$), 4.80(t, 1H, $\diagup\hspace{-0.5em}\diagdown$$_{C\underline{H}-}$), 5.07(bs, 17H, $\diagup\hspace{-0.5em}\diagdown$$_{C\underline{H}-}$), 7.27 & 7.28(each s, 5H, —O—CH$_2$—C$_6$$\underline{H}$$_5$),
7.07-7.93(m, 5H, —SO$_2$C$_6$$\underline{H}$$_5$)

4.19 g of this compound (11) were desulfonylated in the same manner as in Example 1 (using 0.38 g of metallic lithium). In this case, benzyl group elimination occurred simultaneously with desulfonylation, and there were obtained 2.67 g of the compound of general formula (IV) in which n=15 and Z$^2$=—CH$_2$OH, the physical characteristics of which were in agreement with those of the final product obtained in Example 1.

EXAMPLE 13

Following the procedure of Example 1, except that 1.47 g of 4-phenylthio-3-methyl-1-butanol was used in place of 4-phenylsulfonyl-3-methyl-1-butanol and 7.3 ml of a hexane solution of tert-butyllithium (1.5M solution) in place of the hexane solution of n-butyllithium, there were obtained 4.47 g of 4-phenylthio-4-polyprenyl-3-methyl-1-butanol [Compound (12); in general formula (I), n=15, R$^1$=H, R$^2$=—S—C$_6$H$_5$, Z$^1$=—CH$_2$OH], which had the following physical characteristics:

FD-MASS: m/e=1420
IR(cm$^{-1}$): 3325, 1670, 1580, 1380, 1050, 730, 690
$^1$H-NMR($\delta_{ppm}$$^{CDCl3}$):

0.99(d, 3H, CH—C$\underline{H}$$_3$), 1.50(s, 9H, $\diagup\hspace{-0.5em}\diagdown$$^{CH_3}$), 1.60(s, 48H, C$\underline{H}$$_3$$\diagup\hspace{-0.5em}\diagdown$), -continued 2.55–3.0(m, 1H, \CH—S—/), 3.55(t, 2H, —CH₂O—), 4.81(t, 1H, ⟩CH—), 5.07(bs, 17H, ⟩CH—), 6.95–7.40(m, 5H, —S—C₆H₅)

4.40 g of this compound (12) were subjected to reductive elimination of —S—C₆H₅ by the procedure of Example 1 (using 0.44 g of metallic lithium and carrying out the reaction at −50° C.) to give 2.61 g of the compound of general formula (IV) in which n=15 and Z²=—CH₂OH.

EXAMPLE 14

Following the procedure of Example 1, except that 1.59 g of 4-phenylsulfinyl-3-methyl-1-butanol was used in place of 4-phenylsulfonyl-3-methyl-1-butanol, there were obtained 5.31 g of 4-phenylsulfinyl-4-polyprenyl-3-methyl-1-butanol [Compound (13); in general formula (I), n=15, R¹=H, R²=—SO—C₆H₅, Z¹=—CH₂OH], which had the following physical characteristics:
FD-MASS: m/e=1436
IR(cm⁻¹): 3325, 1670, 1580, 1380, 1035, 725, 690
$^1$H-NMR($\delta_{ppm}^{CDCl_3}$):

1.00(d, 3H, \CH—CH₃/), 1.51(s, 9H, CH₃ ⟩), 1.60(s, 48H, CH₃ ⟩), 2.75–3.03(m, 1H, \CH—SO—/), 3.54(t, 2H, —CH₂O—), 4.80(t, 1H, ⟩CH—), 5.07(bs, 17H, ⟩CH—), 7.01–7.68(m, 5H, —SO—C₆H₅)

5.21 g of this compound (13) were subjected to reductive elimination of —SO—C₆H₅ following the procedure of Example 1 (using 0.52 g of metallic lithium and carrying out the reaction at −40° C.) to give 3.49 g of the compound of general formula (IV) in which n=15 and Z²=—CH₂OH.

EXAMPLE 15

Following the procedure of Example 1, except that 2.04 g of 4-phenylsulfonyl-3-methyl-1-butanol dimethyl acetal were used in place of 4-phenylsulfonyl-3-methyl-1-butanol, there were obtained 4.56 g of 4-phenylsulfonyl-4-polyprenyl-3-methyl-1-butanal dimethyl acetal [Compound (14); in general formula (I), n=15, R¹=H, R²=—SO₂C₆H₅, Z¹=—CH(OCH₃)₂], which had the following physical characteristics:
FD-MASS: m/e=1496
IR(cm⁻¹): 1670, 1590
$^1$H-NMR($\delta_{ppm}^{CDCl_3}$):

1.01(d, 3H, \CH—CH₃/), 1.51(s, 9H, CH₃ ⟩), 1.63(s, 48H, CH₃ ⟩), 2.85–3.20(m, 1H, \CH—SO₂—/), 3.20(s, 6H, —OCH₃), 4.31(t, 1H, —OCHO—), 4.81(t, 1H, ⟩CH—), 5.07(bs, 17H, ⟩CH—), 7.32–8.00(m, 5H, —SO₂—C₆H₅)

This compound (14) was desulfonylated by the procedure of Example 1 (using 0.43 g of metallic lithium and carrying out the reaction at −30° C.). The crude product (residue after removal of hexane by distillation under reduced pressure) was dissolved in 200 ml of ethanol, 30 ml of 1N hydrochloric acid added, the mixture stirred at room temperature for 5 hours and then neutralized with aqueous sodium bicarbonate, and most of the ethanol distilled off under reduced pressure. The residue was poured into 200 ml of water and extracted with hexane, and the hexane layer was washed well with water and dried over anhydrous sodium sulfate. The hexane was distilled off under reduced pressure, the residue dissolved in 30 ml of ethanol, 0.5 g of sodium borohydride added, the mixture stirred at room temperature for 4 hours and then poured into 150 ml of water and extracted with hexane, and the hexane layer washed well with water and dried over anhydrous magnesium sulfate. The hexane was distilled off under reduced pressure, and the residue purified by silica gel column chromatography (developing solvent: methylene chloride-ethyl acetate) to give 2.68 g of a colorless, transparent, viscous liquid. The FD-MASS, IR, $^{13}$C-NMR and $^1$H-NMR spectra of this product, which were in agreement with those of the final product obtained in Example 1, demonstrated that this substance was the compound of general formula (IV) in which n=15 and Z²=—CH₂OH.

EXAMPLE 16

Following the procedure of Example 1, except that 2.03 g of 4-phenylsulfonyl-3-methyl-1-butanal ethylene acetal were used in place of 4-phenylsulfonyl-3-methyl-1-butanol, there were obtained 4.86 g of 4-phenylsulfonyl-4-polyprenyl-3-methyl-1-butanal ethylene acetal [Compound (15); in general formula (I), n=15, R¹=H, R²=—SO₂C₆H₅, $Z^1 = -CH\begin{smallmatrix}O\\ \\O\end{smallmatrix}\rceil$, which had the following physical characteristics:
FD-MASS: m/e=1494
IR(cm$^{-1}$): 1670, 1590, 1380, 1150
$^1$H-NMR($\delta_{ppm}^{CDCl_3}$):

1.03(d, 3H, >CH—C$\underline{H}_3$), 1.54(s, 9H, $\overset{CH_3}{\underset{}{\diagup\diagdown}}$), 1.62(s, 48H, C$\underline{H}_3$ $\diagup\diagdown$), 2.83–3.12(m, 1H, >C$\underline{H}$—SO$_2$—), 3.53–3.90(m, 4H, —OC$\underline{H}_2$C$\underline{H}_2$O—), 4.73(t, 1H, —OC$\underline{H}$O—), 4.81(t, 1H, $\diagup\diagdown_{C\underline{H}-}$), 5.08(bs, 17H, $\diagup\diagdown_{C\underline{H}-}$), 7.36–8.00(m, 5H, —SO$_2$—C$_6\underline{H}_5$)

4.80 g of this compound (15) was treated in the same manner as in Example 15 to give 3.16 g of the compound of general formula (IV) in which n=15 and Z$^2$=—CH$_2$OH.

EXAMPLE 17

6.83 g of the polyprenylphenylsulfone of general formula (II) in which n=15 and A=—SO$_2$C$_6$H$_5$ as synthesized in accordance with Reference Example 8 were dissolved in a mixture of 30 ml of anhydrous tetrahydrofuran and 3 ml of anhydrous hexamethylphosphoramide, the mixture cooled to about −10° C. to 0° C., 3.28 ml of a hexane solution of n-butyllithium (1.6M solution) added in a nitrogen atmosphere, the mixture stirred for 15 minutes, and then a solution of 1.51 g of 4-bromo-3-methylbutyl tetrahydropyranyl ether in 2 ml of anhydrous tetrahydrofuran was added dropwise. After the dropping, the mixture was stirred at the same temperature for one hour and then the stirring continued at room temperature (about 20° C.) overnight. Thereafter, the reaction mixture was poured into 200 ml of water and extracted with methylene chloride. The methylene chloride layer was washed with water and dried over anhydrous magnesium sulfate, and the solvent was distilled off under reduced pressure. The slightly yellow liquid thus obtained was purified by silica gel column chromatography (developing solvent: methylene chloride-ethyl acetate) to give 6.91 g of a slightly yellow liquid. The analytical results reported below demonstrated that this product was 4-(1'-phenylsulfonylpolyprenyl)-3-methylbutyl tetrahydropyranyl ether [Compound (16); in general formula (I), n=15, R$^1$=—SO$_2$C$_6$H$_5$, R$^2$=H, $Z^1 = -CH_2-O-\overset{}{\underset{O}{\bigcirc}}]$.

FD-MASS: m/e=1536
IR(cm$^{-1}$): 1660, 1590, 1450, 1380, 1310, 1150, 1090, 1040, 790
$^1$H-NMR($\delta_{ppm}^{CDCl_3}$):

0.70–0.95(m, 3H, >CH—C$\underline{H}_3$), 3.10–4.00

(m, 4H, —C$\underline{H}_2$O), 4.46(bs, 1H, —OC$\underline{H}$O—), 4.75–5.23

(bs, 18H, $\diagup\diagdown_{C\underline{H}-}$), 7.31–7.95(m, 5H, —SO$_2$—C$_6\underline{H}_5$)

6.81 g of this compound (16) were desulfonylated by the procedure of Example 1 (using 0.63 g of metallic lithium) and the protective group removed by the procedure of Example 9, to give 4.10 g of the compound of general formula (IV) in which n=15 and Z$^2$=—CH$_2$OH.

EXAMPLE 18

6.89 g of 4-(1'-phenylsulfonylpolyprenyl)-3-methylbutyl tetrahydropyranyl ether synthesized in the same manner as in Example 17 were dissolved in 200 ml of ethanol, 30 ml of 1N hydrochloric acid added, and the mixture stirred at room temperature for 4 hours. After neutralization with aqueous sodium bicarbonate, most of the ethanol was distilled off under reduced pressure, and the residue poured into 200 ml of water and extracted with hexane. The hexane layer was washed with water and dried over anhydrous magnesium sulfate, the hexane distilled off, and the residue purified by silica gel column chromatography (developing solvent: methylene chloride-ethyl acetate) to give 6.20 g of a colorless or slightly yellow liquid. The analytical results shown below demonstrated that this product was 4-(1'-phenylsulfonylpolyprenyl)-3-methyl-1-butanol [Compound (17); in general formula (I), n=15, R$^1$=—SO$_2$C$_6$H$_5$, R$^2$=H, Z$^1$=—CH$_2$OH].

FD-MASS: m/e=1452
IR(cm$^{-1}$): 3525, 1670, 1590, 1450, 1380, 1310, 1150, 1090
$^1$H-NMR($\delta_{ppm}^{CDCl_3}$): 0.70–0.95(m, 3H, >CH—CH$_3$), 3.44–4.02 (m, 3H, —C$\underline{H}_2$O—, >C$\underline{H}$—SO$_2$—), 4.75–5.25(bs, 18H, $\diagup\diagdown_{C\underline{H}-}$), 7.31–7.90(m, 5H, —SO$_2$C$_6\underline{H}_5$)

6.08 g of this compound (17) were desulfonylated by the procedure of Example 1 (using 0.60 g of metallic lithium) to give 4.09 g of the compound of general formula (IV) in which n=15 and Z$^2$=—CH$_2$OH.

EXAMPLES 19-24

Using the compounds of general formula (II) and the compounds of general formula (III) respectively specified in Table 2 in the amounts also specified in said Table, the procedure of Example 17 was followed to synthesize the corresponding compounds of general formula (I). The compounds of general formula (I) thus obtained were respectively treated by the procedures specified in Table 2 to give the compound of general formula (IV) in which n=15 and $Z^2$=—$CH_2OH$. The yields of the compounds of general formula (i), the yields of the compound of general formula (IV), etcetera, are summarized in Table 4. The physical characteristics of the compounds of general formula (I) synthesized herein were as follows:

4-(1'-Phenylsulfonylpolyprenyl)-3-methyl-1-butyl benzyl ether [Compound (18)]

FD-MASS: m/e=1542
IR(cm$^{-1}$): 1660, 1580, 1500, 1450, 1300, 1140, 1100, 740, 700
$^1$H-NMR($\delta_{ppm}^{CDCl_3}$): 0.70–0.93(m, 3H, >CH—C$\underline{H}_3$), 3.24–3.53 (m, 2H, —C$\underline{H}_2$O—), 3.67–4.00(m, 1H, >C$\underline{H}$—SO$_2$—),

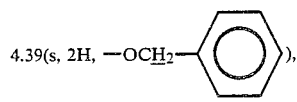
4.39(s, 2H, —OC$\underline{H}_2$—⟨⟩), 4.74–5.24(bs, 18H, 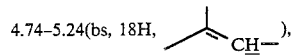), 7.06–7.90(m, 5H, —SO$_2$—C$_6$$\underline{H}_5$), 7.27(s, 5H, —CH$_2$C$_6$$\underline{H}_5$)

4-(1'-Phenylsulfonylpolyprenyl)-3-methyl-1-butyl acetate [Compound (19)]

FD-MASS: m/e=1494
IR(cm$^{-1}$): 1740, 1660, 1590, 1450, 1300, 1240, 1150, 1090
$^1$H-NMR($\delta_{ppm}^{CDCl_3}$): 0.73–0.98(m, 3H, >CH—C$\underline{H}_3$), 1.98(s, 3H, $$\underset{OCC\underline{H}_3)}{\overset{O}{\|}}$$

3.64–4.17(m, 3H, —C$\underline{H}_2$O—, >C$\underline{H}$—SO$_2$—), 4.74–5.24(bs, 18H, ), 7.32–7.93(m, 5H, —SO$_2$—C$_6$$\underline{H}_5$)

4-(1'-Phenylsulfinylpolyprenyl)-3-methylbutyl tetrahydropyranyl ether [Compound (20)]

FD-MASS: m/e=1520
IR(cm$^{-1}$): 1670, 1590, 1440, 1300, 1150, 1080, 1035, 740, 690
$^1$H-NMR($\delta_{ppm}^{CDCl_3}$): 0.72–0.98(m, 3H, >CH—C$\underline{H}_3$), 2.73–4.10(m, 5H, —C$\underline{H}_2$O—, >C$\underline{H}$—SO—), 4.43(bs, 1H, —OC$\underline{H}$O—), 4.75–5.26(bs, 18H, ), 7.00–7.69(m, 5H, —SO—C$_6$$\underline{H}_5$)

4-(1'-Phenylthiopolyprenyl)-3-methylbutyl tetrahydropyranyl ether [Compound (21)]

FD-MASS: m/e=1504
IR(cm$^{-1}$): 1670, 1590, 1450, 1150, 1075, 1040, 740, 690
$^1$H-NMR ($\delta_{ppm}^{CDCl_3}$): 0.71–0.96(m, 3H, >CH—C$\underline{H}_3$), 3.10–4.00 (m, 5H, —C$\underline{H}_2$O—, >C$\underline{H}$—S—), 4.47(bs, 1H, —OC$\underline{H}$O—), 4.70–5.26(bs, 18H, 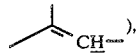), 6.95–7.40(m, 5H, —S—C$_6$$\underline{H}_5$)

4-[1'-(2-Pyridyl)thiopolyprenyl]-3-methylbutyl tetrahydropyranyl ether [Compound (22)]

FD-MASS: m/e=1505
IR(cm$^{-1}$): 1670, 1580, 1460, 1420, 1300, 1150, 1130, 1080
$^1$H-NMR($\delta_{ppm}^{CDCl_3}$): 0.70–0.98(m, 3H, >CH—C$\underline{H}_3$), 3.15–4.02 (m, 5H, —C$\underline{H}_2$O—, —S—C$\underline{H}$>), 4.46(bs, 1H, —OC$\underline{H}$O—), 4.71–5.25(bs, 18H, 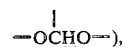), 6.75–8.45(m, 4H, —S—C$_5$$\underline{H}_4$N)

4-[1'-(2-Thiazolinyl)-thiopolyprenyl]-3-methylbutyl tetrahydropyranyl ether [Compound (23)]

FD-MASS: m/e=1513
IR(cm$^{-1}$): 1660, 1570, 1300, 1150, 1080, 1040, 1000, 960, 920, 790
$^1$H-NMR($\delta_{ppm}^{CDCl_3}$): 0.70–0.98(m, 3H, >CH—C$\underline{H}_3$), 3.10–4.00 (m, 7H, —C$\underline{H}_2$O—, >C$\underline{H}$—S—, either —C$\underline{H}_2$ in —SC$\underline{H}_2$CH$_2$N—), 4.15(t, 2H, either —C$\underline{H}_2$ in —SCH$_2$C$\underline{H}_2$N—), 4.46(bs, 1H, —OC$\underline{H}$O—), 4.76–5.25(bs, 18H), 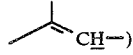

TABLE 2

| Ex. No. | Compound of general formula (II) | | | Compound No. | n | Compound of general formula (III) | | | Amount (g) | Compound of general formula (I) | | | | | Yield (g) | Amount* (g) | Compound of general formula (IV)** | | Yield (g) |
|---|---|---|---|---|---|---|---|---|---|---|---|---|---|---|---|---|---|---|---|
| | n | A | Amount (g) | | | X | $Z^1$ | | | $R^1$ | $R^2$ | $Z^1$ | | | | | Procedure** | | |
| 19 | 15 | –SO$_2$–C$_6$H$_5$ | 6.83 | (18) | 15 | Br | –CH$_2$OCH$_2$–C$_6$H$_5$ | | 1.40 | –SO$_2$–C$_6$H$_5$ | H | –CH$_2$OCH$_2$–C$_6$H$_5$ | | | 6.55 | 6.50 | Same as Ex. 12 | | 4.31 |
| 20 | 15 | –SO$_2$–C$_6$H$_5$ | 6.83 | (19) | 15 | Br | –CH$_2$OCCH$_3$ (C=O) | | 1.25 | –SO$_2$–C$_6$H$_5$ | H | –CH$_2$OCCH$_3$ (C=O) | | | 6.13 | 6.08 | Same as Ex. 23 | | 3.46 |
| 21 | 15 | –SO–C$_6$H$_5$ | 6.75 | (20) | 15 | Br | –CH$_2$O-(tetrahydropyranyl) | | 1.51 | –SO–C$_6$H$_5$ | H | –CH$_2$O-(tetrahydropyranyl) | | | 5.93 | 5.83 | Same as Ex. 9 | | 3.71 |
| 22 | 15 | –S–C$_6$H$_5$ | 6.67 | (21) | 15 | Br | –CH$_2$O-(tetrahydropyranyl) | | 1.51 | –S–C$_6$H$_5$ | H | –CH$_2$O-(tetrahydropyranyl) | | | 6.17 | 6.10 | Same as Ex. 9 | | 3.86 |
| 23 | 15 | –S-(2-pyridyl) | 6.68 | (22) | 15 | Br | –CH$_2$O-(tetrahydropyranyl) | | 1.51 | –S-(2-pyridyl) | H | –CH$_2$O-(tetrahydropyranyl) | | | 6.10 | 6.00 | Same as Ex. 9 | | 3.80 |
| 24 | 15 | –S-(thiazolinyl) | 6.66 | (23) | 15 | Br | –CH$_2$O-(tetrahydropyranyl) | | 1.51 | –S-(thiazolinyl) | H | –CH$_2$O-(tetrahydropyranyl) | | | 5.14 | 5.09 | Same as Ex. 9 | | 2.95 |

*Amount used for the production of compound of general formula (IV).
**Procedure used for the production of compound (IV) from compound (I).

While in the description immediately above, the synthesis of the compounds of general formulae (I) and (IV) in which n=15 was described by way of example, homologs thereof, namely compounds of general formulae (I) and (IV) in which n=11 to 19, exclusive of 15, could be synthesized in analogous manner. The characteristic absorptions in IR spectra and the characteristic signals in $^1$H-NMR spectra of such homologs in which n≠15, with respect to the locations thereof, were in agreement with those of the homolog in which n=15, and the m/e values for those homologs as obtained from FD-MASS analysis differed from that for the homolog in which n=15 by values corresponding to the differences in the number of isoprene units.

EXAMPLE 25

2.0 g of (S)-4-bromo-3-methylbutyl benzyl ether ($[\alpha]_D^{20}+6.05°$, c=1.10, $C_2H_5OH$) were dissolved in 20 ml of dried dimethylformamide, then 2.56 g of anhydrous sodium phenylsulfinate added, the mixture stirred at 50°–55° C. for 16 hours and then at 65°–70° C. for 1.5 hours and poured into 200 ml of water, followed by extraction with methylene chloride. The extract was washed well with water and dried over anhydrous magnesium sulfate. The methylene chloride was distilled off under reduced pressure, and the residue purified by silica gel column chromatography (developing solvent: ethyl acetate-methylene chloride) to give 2.14 g of a colorless liquid. The characteristic signals shown below of its $^1$H-NMR spectrum demonstrated that this substance was 4-phenylsulfonyl-3-methylbutyl benzyl ether.

$^1$H-NMR($\delta_{ppm}^{CDCl_3}$):

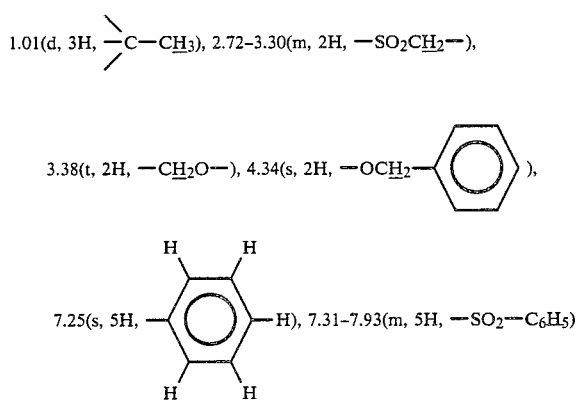

A polyprenyl bromide mixture was prepared by reacting a mixture of polyprenols of general formula (V) in which n=11 to 19 as obtained in accordance with Reference Example 1 (to follow) with substantially the same composition as described in Reference Example 1 with phosphorus tribromide in accordance with Reference Example 2 (to be described later). 6.52 g of the polyprenyl bromide mixture were reacted with 1.91 g of the above-mentioned 4-phenylsulfonyl-3-methylbutyl benzyl ether by the procedure of Example 1 and the reaction mixture treated in the same manner as in Example 1 to give 4.20 g of a colorless to slightly yellow, viscous liquid. The characteristic absorptions in the IR spectrum and the characteristic signals in the $^1$H-NMR spectrum of the liquid were in agreement with those of Compound (11) synthesized in Example 12 in their locations, whereby it was confirmed that this substance was 4-phenylsulfonyl-4-polyprenyl-3-methylbutyl benzyl ether (in general formula (I) $C_6H_5$, $R^1$=H, $R^2$=—$SO_2C_6H_5$, $Z^1$=—$CH_2OCH_2C_6H_5$.

4.00 g of this viscous liquid were treated for desulfonylation (and for simultaneous protective group elimination) by the procedure of Example 1 to give 3.12 g of a colorless, transparent liquid. This liquid was subjected to high performance liquid chromatography using a Merck semipreparative high performance liquid chromatography column LiChrosorb RP18-10 ($C_{18}$type) with a 90:10 acetone-methanol mixed solvent as the eluent and a differential refractometer as the detector, whereby 9 main peaks were confirmed. The relative amounts in percentage were calculated from the area proportions readable on the chromatogram. The values obtained are reported below.

| Peak No. | Value of n | % Amount | FD-MASS |
|---|---|---|---|
| 1 | 11 | 0.3 | 1040 |
| 2 | 12 | 1.0 | 1108 |
| 3 | 13 | 5.9 | 1176 |
| 4 | 14 | 25.7 | 1244 |
| 5 | 15 | 39.6 | 1312 |
| 6 | 16 | 19.3 | 1380 |
| 7 | 17 | 5.7 | 1448 |
| 8 | 18 | 1.7 | 1516 |
| 9 | 19 | 0.8 | 1584 |

The respective fractions were isolated by the same liquid chromatography and submitted to FD-MASS analysis, whereby it was confirmed that the peaks corresponded to n=11 through 19, respectively. IR, $^1$H-NMR and $^{13}$C-NMR analyses were performed for the fractions corresponding to the respective peaks and it was confirmed that the fractions were compounds of general formula (IV) in which n=11–19 and $Z^2$=—$CH_2OH$. The compound which corresponded to peak No. 5 and in which n=15 gave quite the same analytical results as those for the final product obtained in Example 1. Regarding the other peak fractions, corresponding IR, $^1$H-NMR and $^{13}$C-NMR signals appeared in the same positions with slight differences in the relative intensity. The optical rotation of the liquid obtained was $[\alpha]_D^{20}=+0.51°$ (neat).

EXAMPLE 26

Following the procedure of Example 25, except that (R)-4-bromo-3-methylbutyl benzyl ether ($[\alpha]_D^{20}=-6.05°$, c=1.10, $C_2H_5OH$) was used in place of (S)-4-bromo-3-methylbutyl benzyl ether, an optically active 4-phenylsulfonyl-4-polyprenyl-3-methylbutyl benzyl ether mixture was synthesized and this was treated in the same manner for simultaneous desulfonylation and protective group elimination to give a liquid having an optical rotation of $[\alpha]_D^{20}=-0.51°$ (neat). Analytical results demonstrated that this liquid was a mixture of compounds of general formula (IV) in which n=11 to 19 and $Z^2$=$CH_2OH$.

REFERENCE EXAMPLE 1

Separation of polyprenol

Ten kilograms (in the undried state) of leaves of Ginkgo biloba, which were collected in Kurashiki City, Japan at the end of October, were dried with hot air at about 40° C. for 24 hours, and then extracted with 80 liters of chloroform at about 15° C. for 7 days. The chloroform was removed from the extract and 5 liters of petroleum ether were added to the concentrate. The insoluble matter was separated by filtration. The filtrate was concentrated and chromatographed on a silica gel column using chloroform as an eluent to separate a fraction having an Rf value of 0.50 and 0.19 as determined by silica gel thin-layer chromatography (TLC plate Merck silica 60F$_{254}$ precoated, layer thickness 0.25 mm, developed 10 cm) using a mixed solvent of n-hexane-ethyl acetate (9:1 by volume) as a developing solvent. There were obtained about 37 g of an oil. In the above thin-layer chromatography, solanesly acetate had an Rf of 0.41. About 400 ml of acetone were added to the oil to dissolve acetone-soluble components. The insoluble matter was filtered off, and the filtrate was concentrated. The oil obtained was heated at 65° C. for 2 hours together with 400 ml of methanol, 40 ml of water and 20 g of sodium hydroxide. The methanol was then distilled off and diethyl ether (500 ml) was added to the residue for extraction. The ether layer was washed five times with about 100 ml of water and dried over anhydrous sodium sulfate. The solvent was distilled off to give 24.2 g of an oil.

The oil was then chromatographed on a column of about 1 kg of silica gel using a mixture of n-hexaneisopropyl ether (90:10 by volume) as the eluent to separate a fraction having an Rf value of 0.19 as determined by the same thin-layer chromatography as described above, whereby 21.8 g of an oil were obtained. The oil was a polyprenol fraction having a purity of more than 95%. This was analyzed by high-performance liquid chromatography using a Merck semipreparative high-performance liquid chromatography column (C$_{18}$ type) RP18-10 with a mixed solvent of acetone-methanol (90:10 by volume) as the developing solvent and a differential refractometer as the detector, and the area proportions of the individual peaks in the resulting chromatography were determined. The following results were obtained.

| Peak No. | Number of cis-isoprene units(n) | Area proportion (%) |
|---|---|---|
| 1 | 11 | 0.3 |
| 2 | 12 | 1.1 |
| 3 | 13 | 5.9 |
| 4 | 14 | 25.6 |
| 5 | 15 | 39.4 |
| 6 | 16 | 19.2 |
| 7 | 17 | 5.9 |
| 8 | 18 | 1.8 |
| 9 | 19 | 0.8 |

The individual components were separated from the above oily product (containing more than 95% of polyprenols) by using the same high-performance liquid chromatography column as mentioned above. By mass spectroscopy, infrared absorption spectroscopy, $^1$H-NMR spectroscopy and $^{13}$C-NMR spectroscopy, these compounds were identified to be polyprenols having the structure represented by general formula (V).

The results of FD-MASS of these components and their δ values in $^1$H-NMR spectra are summarized in Table 3. The δ values of these components in $^{13}$C-NMR spectra are summarized in Table 4.

In the $^1$H-NMR data, (b) represents a broad signal; (d), a doublet signal; and (t), a triplet signal.

TABLE 3

| n (number of cis-isoprene units) | FD-MASS (m/e) Found | FD-MASS (m/e) Cald. | =CHCH$_2$OH | =CH— | —CH$_2$OH | —CH$_2$— | H$_3$C\\=/H / —CH$_2$ CH$_2$OH | H$_3$C\\=/H / —CH$_2$ CH$_2$— | H$_3$C\\=/CH$_2$— / —CH$_2$ H |
|---|---|---|---|---|---|---|---|---|---|
| 11 | 970 | 970 | 5.44 (t) | 5.13 (b) | 4.08 (d) | 2.04 (b) | 1.74 | 1.68 | 1.60 |
| 12 | 1038 | 1038 | 5.44 (t) | 5.12 (b) | 4.08 (d) | 2.04 (b) | 1.74 | 1.68 | 1.60 |
| 13 | 1106 | 1106 | 5.43 (t) | 5.12 (b) | 4.08 (d) | 2.04 (b) | 1.74 | 1.68 | 1.60 |
| 14 | 1174 | 1174 | 5.44 (t) | 5.12 (b) | 4.08 (d) | 2.04 (b) | 1.74 | 1.68 | 1.60 |
| 15 | 1242 | 1242 | 5.44 (t) | 5.13 (b) | 4.08 (d) | 2.04 (b) | 1.74 | 1.68 | 1.60 |
| 16 | 1310 | 1310 | 5.44 (t) | 5.14 (b) | 4.08 (d) | 2.04 (b) | 1.74 | 1.68 | 1.60 |
| 17 | 1378 | 1378 | 5.44 (t) | 5.13 (b) | 4.08 (d) | 2.04 (b) | 1.74 | 1.68 | 1.60 |
| 18 | 1446 | 1446 | 5.43 (t) | 5.13 (b) | 4.08 (d) | 2.05 (b) | 1.74 | 1.68 | 1.60 |
| 19 | 1514 | 1514 | 5.44 (t) | 5.13 (b) | 4.08 (d) | 2.04 (b) | 1.74 | 1.68 | 1.60 |

TABLE 4

| n (number of cis-isoprene units) | \\C= / | =CH— | —CH$_2$OH | CH$_3$\\=/ /CH$_2$ | CH$_3$\\=/ /CH$_2$ | CH$_3$\\=/CH$_3$ /CH$_2$ | CH$_3$\\=/CH$_3$ /CH$_2$ | CH$_3$\\=/CH$_3$ /CH$_2$ |
|---|---|---|---|---|---|---|---|---|
| 11 | 135.17 | 125.09 | 59.00 | 39.77 | 32.27 | 32.04 | | |
| 12 | 135.17 | 125.10 | 58.99 | 39.78 | 32.28 | 32.05 | | |
| 13 | 135.16 | 125.08 | 58.99 | 39.78 | 32.27 | 32.05 | | |
| 14 | 135.17 | 125.09 | 59.00 | 39.77 | 32.27 | 32.04 | | |
| 15 | 135.15 | 125.12 | 58.99 | 39.78 | 32.29 | 32.05 | | |
| 16 | 135.15 | 125.11 | 58.98 | 39.77 | 32.28 | 32.05 | | |
| 17 | 135.15 | 125.12 | 59.00 | 39.77 | 32.29 | 32.05 | | |
| 18 | 135.16 | 125.10 | 58.98 | 39.77 | 32.29 | 32.05 | | |
| 19 | 135.15 | 125.10 | 58.98 | 39.78 | 32.28 | 32.05 | | |

| n (number of cis-isoprene units) | CH$_3$\\=/ /CH$_2$— | CH$_3$\\=/H /CH$_3$ | CH$_3$\\=/H /CH$_3$ | CH$_3$\\=/ /H |

TABLE 4-continued

| | | | | | |
|---|---|---|---|---|---|
| 11 | 26.47 | 23.42 | 25.67 | 17.64 | 15.98 |
| 12 | 26.47 | 23.42 | 25.66 | 17.64 | 15.98 |
| 13 | 26.48 | 23.42 | 25.67 | 17.65 | 15.99 |
| 14 | 26.47 | 23.42 | 25.66 | 17.64 | 15.97 |
| 15 | 26.49 | 23.42 | 25.65 | 17.65 | 15.99 |
| 16 | 26.49 | 23.42 | 25.65 | 17.64 | 15.98 |
| 17 | 26.49 | 23.41 | 25.66 | 17.65 | 15.99 |
| 18 | 26.48 | 23.41 | 25.64 | 17.64 | 15.99 |
| 19 | 26.49 | 23.42 | 25.65 | 17.65 | 15.98 |

REFERENCE EXAMPLE 2

Synthesis of polyprenyl bromide 12.4 g of polyprenol of general formula (V) in which n=15 and 1 ml of pyridine were added to 200 ml of n-hexane. To the resulting solution were added dropwise 2.0 g of phosphorus tribromide in an atmosphere of nitrogen. After the addition, the mixture was stirred overnight at room temperature in an atmosphere of nitrogen. The n-hexane solution was transferred to a separating funnel, washed ten times with about 50 ml of water and then dried over anhydrous magnesium sulfate. The n-hexane was distilled off to give 12.0 g of a slightly yellow liquid product. NMR spectroscopy of this product revealed that the signal (doublet, $\delta=4.08$) assignable to the —CH$_2$OH group of the starting polyprenol had disappeared and a signal (doublet, $\delta=3.91$) assignable to —CH$_2$Br had newly appeared. FD-MASS analysis of this liquid product gave m/e=1304. Based on these analytical data, the above product was identified to be polyprenyl bromide of general formula (II) in which n=15 and A=Br.

By a procedure similar to that described above, polyprenyl bromide species in which n was other than 15 and polyprenyl bromide mixtures having various compositions with n being distributed in the range of 11–19 were synthesized.

REFERENCE EXAMPLE 3

Synthesis of polyprenyl chloride 12.4 g of polyprenol of general formula (V) in which n is 15 and 1.0 ml of pyridine were added to 200 ml of n-hexane. To the resulting solution was added dropwise 1.5 g of thionyl chloride at room temperature in an atmosphere of nitrogen. After the addition, the mixture was further stirred at room temperature for 2 hours. The reaction mixture was then worked up in the same manner as in Reference Example 2 to give 11.2 g of a pale yellow liquid. IR analysis of the liquid showed that the absorption attributable to the —OH group of the starting polyprenol had disappeared. NMR analysis demonstrated that the signal assignable to —CH$_2$OH of the starting polyprenol had disappeared and a signal (doublet, $\delta=3.95$) assignable to —CH$_2$Cl had newly appeared. FD-MASS analysis gave m/e=1260. From these analytical data, the above product was identified to be polyprenyl chloride of general formula (II) in which n=15 and A=Cl.

By a procedure similar to that described above, polyprenyl chloride species in which n was other than 15 and polyprenyl chloride mixtures having various compositions with n being distributed in the range of 11–19 were synthesized.

REFERENCE EXAMPLE 4

Synthesis of polyprenyl phenyl sulfide 2.2 g of thiophenol and 2.8 g of potassium carbonate were added to 50 ml of dimethylformamide and, with stirring at about 20° C., 13.0 g of polyprenyl bromide of general formula (II) in which n=15 and A=Br were added dropwise. After the addition, the mixture was stirred overnight at room temperature. The reaction mixture was poured into about 100 ml of water and extracted with hexane. The hexane layer was washed with a 10% aqueous solution of sodium hydroxide and water, and then dried over anhydrous magnesium sulfate. The hexane was distilled off to give a yellow liquid. The yellow liquid was purified by silica gel column chromatography using methylene chloride as the eluent to give 8.6 g of a slightly yellow liquid. NMR analysis of this liquid showed that a signal (doublet, $\delta=3.91$) assignable to —CH$_2$Br of the starting polyprenyl bromide had disappeared and a signal (doublet, $\delta=3.47$) assignable to —CH$_2$S— and a signal (multiplet, $\delta=7.05$–7.32) assignable to —SC$_6$H$_5$ had newly appeared. FD-MASS analysis gave m/e=1334.

Based on these analytical data, the liquid product was identified to be polyprenyl phenyl sulfide of general formula (II) in which n=15 and A=—SC$_6$H$_5$.

By a procedure similar to that described above, polyprenyl phenyl sulfide species in which n was other than 15 and polyprenyl phenyl sulfide mixtures having various compositions with n being distributed in the range of 11–19 were synthesized.

REFERENCE EXAMPLE 5

Synthesis of polyprenyl 2-thiazolinyl sulfide 4.05 g of 2-mercaptothiazoline and 1.44 g of 50% sodium hydride were added to 45 ml of dimethylformamide, and the mixture was stirred at room temperature for 1 hour. A solution of 19.5 g of polyprenyl bromide of general formula (II) in which n=15 and A=Br in 15 ml of dimethylformamide was added dropwise. After the addition, the mixture was stirred overnight at room temperature. The reaction mixture was poured into about 150 ml of water and extracted with diethyl ether. The extract was washed with water, dried and concentrated to give a yellow liquid. The liquid was purified by silica gel column chromatography using hexane-ethyl acetate as the eluent to give 8.4 g of a slightly yellow liquid. NMR analysis of this liquid demonstrated that the signal (doublet, $\delta=3.91$) assignable to —CH$_2$Br of the starting polyprenyl bromide had disappeared and signals (doublet, $\delta=3.74$) assignable to —CH$_2$S and signals (triplet, $\delta=3.32$ and triplet, $\delta=4.16$) assignable to

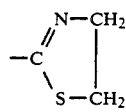

had newly appeared. FD-MASS analysis of this liquid gave m/e=1343. From the above analytical data, this liquid was identified to be polyprenyl 2-thiazolinyl sulfide of general formula (II) in which n=15 and

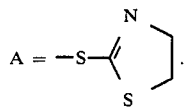

By a procedure similar to that described above, polyprenyl 2-thiazolinyl sulfide species in which n was other than 15 and polyprenyl 2-thiazolinyl sulfide mixtures having various compositions with n being distributed in the range of 11–19 were synthesized.

REFERENCE EXAMPLE 6

Synthesis of polyprenyl 2-pyridyl sulfide 2.22 g of 2-mercaptopyridine and 0.96 g of 50% sodium hydride were dissolved in 50 ml of dimethylformamide, and the mixture was stirred at room temperature for one hour. Thereafter, 13.0 g of polyprenyl bromide of general formula (II) in which n=15 and A=Br were added. After the addition, the mixture was stirred overnight at room temperature. The reaction mixture was poured into about 50 ml of water and extracted with diethyl ether. The diethyl ether layer was washed with water and dried over anhydrous magnesium sulfate. The ether was distilled off to give a yellow liquid. The liquid was purified by silica gel column chromatography using hexane-ethyl acetate as the eluent to give 7.8 g of a slightly yellow liquid. NMR analysis of this liquid demonstrated that the signal (doublet, $\delta=3.91$) assignable to $-CH_2Br$ of the starting polyprenyl bromide had disappeared and a signal (doublet, $\delta=3.78$) assignable to $-CH_2S$ and a signal (multiplet, $\delta=6.75-8.35$) assignable to $-S-C_5H_4N$ had newly appeared. FD-MASS of this liquid gave m/e=1335.

Based on the above analytical data, this liquid was identified to be polyprenyl 2-pyridyl sulfide of general formula (II) in which n=15 and A=—$SC_5H_4N$.

By a procedure similar to that described above, polyprenyl 2-pyridyl sulfide species in which n was other than 15 and polyprenyl 2-pyridyl sulfide mixtures having various compositions with n being distributed in the range of 11–19 were synthesized.

REFERENCE EXAMPLE 7

Synthesis of polyprenyl phenyl sulfoxide 8.47 g of polyprenyl phenyl sulfide of general formula (II) in which n=15 and A=$SC_6H_5$ were dissolved in 65 ml of methanol, and a solution of 1.64 g of sodium metaperiodate in 32 ml of water was added. The mixture was stirred overnight at room temperature. An aqueous solution of sodium chloride was added to the reaction mixture, and the resulting mixture was extracted with diethyl ether. The ether layer was washed with water and a saturated aqueous solution of sodium chloride, and dried over anhydrous magnesium sulfate. The ether was distilled off to give a yellow liquid. The liquid was purified by silica gel column chromatography using hexane-diethyl ether as the eluent to give 6.75 g of purified liquid. IR analysis of this purified liquid demonstrated that a strong absorption at 1035 cm$^{-1}$ attributable to a sulfoxide group which was absent in the starting polyprenyl phenyl sulfide had appeared. In the NMR spectrum, a signal (doublet, $\delta=3.47$) assignable to $-CH_2SC_6H_5$ of the starting polyprenyl phenyl sulfide had disappeared, and a signal (doublet, $\delta=3.35$) assignable to $-CH_2SOC_6H_5$ had appeared. FD-MASS analysis gave m/e=1350. From the above analytical data, this liquid was identified to be polyprenyl phenyl sulfoxide of general formula (II) in which n=15 and A=—$SOC_6H_5$.

By a procedure similar to that described above, polyprenyl phenyl sulfoxide species in which n was other than 15 and polyprenyl phenyl sulfoxide mixtures with various compositions with n being distributed in the range of 11–19 were synthesized.

REFERENCE EXAMPLE 8

Synthesis of polyprenyl phenyl sulfone 13.0 g of polyprenyl bromide of general formula (II) in which n=15 and A=Br were dissolved in a mixture of 100 ml of N,N-dimethylformamide and 100 ml of tetrahydrofuran, and 3.3 g of sodium phenylsulfinate was added. The mixture was stirred at room temperature for 17 hours and then at 50° C. for 1 hour. The solvent was removed using a rotary evaporator, and water was added to the reaction mixture, followed by extraction with benzene. The benzene layer was washed with water and dried over anhydrous magnesium sulfate. Removal of the solvent gave a yellow liquid. The liquid was purified by silica gel column chromatography using hexane-ethyl acetate as the eluent to give 9.4 g of a pale yellow liquid. $^1$H-NMR analysis of this liquid demonstrated that the signal (doublet, $\delta=3.91$) assignable to $-CH_2Br$ of the starting polyprenyl bromide had disappeared and a signal (doublet, $\delta=3.77$) assignable to $-CH_2SO_2C_6H_5$ and a signal (multiplet, $\delta=7.31-7.93$) assignable to $-SO_2C_6H_5$ had newly appeared. FD-MASS analysis of the liquid gave m/e=1366. From these analytical data, this liquid was identified to be a compound of general formula (II) in which n=15 and A=—$SO_2C_6H_5$.

By a procedure similar to that described above, polyprenyl phenyl sulfone species in which n was other than 15 and polyprenyl phenyl sulfone mixtures having various compositions with n being distributed in the range of 11–19 were synthesized.

REFERENCE EXAMPLE 9

Synthesis of 4-phenylthio-3-methyl-1-butanol 17.2 g of 3-methyl-3-buten-1-ol, 11.0 g of benzenethiol and 0.5 g of azobisisobutyronitrile were added to 50 ml of benzene. After stirring at the refluxing point of benzene in a nitrogen atmosphere for 5 hours, the solvent was distilled off, and the concentrate was purified by silica gel column chromatography (developing solvent: methylene chloride-ethyl acetate) to give 14.7 g of a slightly yellow liquid. The characteristic signals of this liquid as found on its $^1$H-NMR spectrum were as follows:

$^1$H-NMR($\delta_{ppm}^{CDCl_3}$): 0.98(d, 3H,

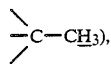

2.56–3.02(m, 2H, —SCH₂—), 3.57(t, 2H, —CH₂O—), 6.94–7.38(m, 5H, SC₆H₅)

The above data evidenced that the slightly yellow liquid was 4-phenylthio-3-methyl-1-butanol of the formula

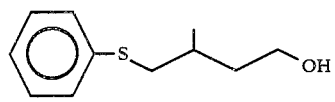

REFERENCE EXAMPLE 10

Synthesis of 4-phenylsulfinyl-3-methyl-1-butanol 1.96 g of 4-phenylthio-3-methyl-1-butanol were dissolved in 100 ml of methanol, a solution of 2.57 g of sodium metaperiodate in 50 ml of water added, and the mixture stirred at room temperature overnight. Then, an aqueous solution of sodium chloride was added, the resulting mixture extracted with diethyl ether, the ether layer washed with water and a saturated aqueous solution of sodium chloride and dried over anhydrous magnesium sulfate, and the ether distilled off. There was obtained a slightly yellow liquid. This was purified by silica gel column chromatography (developing solvent: methylene chloride-ethyl acetate) to give 1.60 g of a colorless to slightly yellow liquid. The characteristic signals of this substance on its ¹H-NMR spectrum were as follows:

¹H-NMR($\delta_{ppm}^{CDCl_3}$): 1.00(d, 3H,

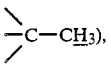

2.66–3.15(m, 2H, —SOCH₂—), 3.55(t, 2H, —CH₂O—), 7.02–7.66(m, 5H, —SOC₆H₅)

The above data evidenced that the liquid was 4-phenylsulfinyl-3-methyl-1-butanol of the formula

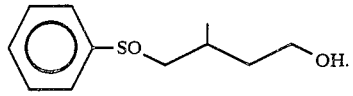

REFERENCE EXAMPLE 11

Synthesis of 4-phenylsulfonyl-3-methyl-1-butanol 11.6 g of m-chloroperbenzoic acid were added to 150 ml of methylene chloride. Thereto was added dropwise a solution of 5.0 g of 4-phenylthio-3-methyl-1-butanol in 50 ml of methylene chloride gradually with stirring and cooling to 0° C. After the dropping, stirring was continued at 0° C. for one hour. The precipitate consisting of m-chlorobenzoic acid was filtered off, 100 ml of 10% (by weight) aqueous sodium hydroxide added to the filtrate, and the resulting mixture stirred at room temperature for 30 minutes. Then, the methylene chloride layer was separated, washed with water and dried over anhydrous magnesium sulfate, the methylene chloride distilled off, and the concentrate thus obtained purified by silica gel chromatography (developing solvent: methylene chloride-ethyl acetate) to give 5.82 g of a colorless liquid. This demonstrated the following characteristic signals on its ¹H-NMR spectrum:

¹H-NMR($\delta_{ppm}^{CDCl_3}$): 1.00(d, 3H,

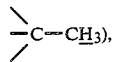

2.77–3.30(m, 2H, —SO₂CH₂—), 3.54(t, 2H, —CH₂O—), 7.25–7.96(m, 5H, SO₂C₆H₅)

The above data demonstrated that said liquid was 4-phenylsulfonyl-3-methyl-1-butanol of the formula

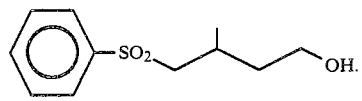

REFERENCE EXAMPLE 12

Synthesis of 4-phenylsulfonyl-3-methyl-1-butanal ethylene acetal 4 g of chromic anhydride were slowly added to 12 ml of hexamethylphosphoramide, and the mixture stirred at room temperature for one hour. Then, a solution of 4.56 g of 4-phenylsulfonyl-3-methyl-1-butanol in 6 ml of hexamethylphosphoramide was added gradually, and the resulting mixture stirred at room temperature for 6 hours, then poured into 100 ml of water and extracted with diethyl ether. The ether layer was washed with aqueous sodium bicarbonate and water and dried over anhydrous sodium sulfate, and then the ether distilled off. The residue was dissolved in 100 ml of benzene. Thereto were added 20 ml of ethylene glycol and 0.1 g of p-toluenesulfonic acid, and dehydration treatment was carried out under reflux. The contents were poured into 100 ml of water, and the benzene layer separated, washed with aqueous sodium bicarbonate and water and then dried over anhydrous sodium sulfate. The benzene was distilled off under reduced pressure, and the residue purified by silica gel chromatography (developing solvent: methylene chloride-ethyl acetate) to give 3.20 g of a colorless liquid. The characteristic signals found on its ¹H-NMR spectrum and reported below evidenced that this substance was 4-phenylsulfonyl-3-methyl-1-butanal ethylene acetal of the formula

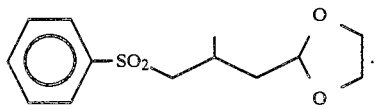

¹H-NMR($\delta_{ppm}^{CDCl_3}$): 1.08(d, 3H, >CH—CH₃), 2.74–3.48(m, 2H, —SO₂—CH₂—), 3.55–3.94(m, 4H, —OCH₂CH₂O—), 4.76(t, 1H,

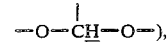

7.40–8.04(m, 5H, SO₂C₆H₅)

REFERENCE EXAMPLE 13

Synthesis of 4-phenylsulfonyl-3-methyl-1-butanal dimethyl acetal

The procedure of Reference Example 12 was repeated, except that 30 ml of methanol were used in place of ethylene glycol (20 ml). There were obtained 2.51 g of a colorless liquid. The characteristic signals on its $^1$H-NMR spectrum as reported below demonstrated that this substance was 4-phenylsulfonyl-3-methyl-1-butanal dimethyl acetal.

$^1$H-NMR($\delta_{ppm}^{CDCl_3}$): 1.05(d, 3H, >CH—C$\underline{H}_3$), 2.72–3.50(m, 2H, —SO$_2$C$\underline{H}_2$—), 3.22(s, 6H, —OC$\underline{H}_3$), 4.32(t, 1H,

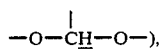

), 7.40–8.05(m, 5H, SO$_2$C$_6$$\underline{H}_5$)

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A polyprenyl compound having the general formula:

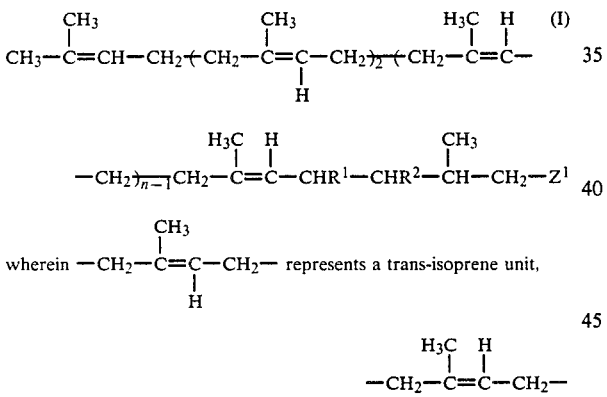

wherein —CH$_2$—C(CH$_3$)=CH—CH$_2$— represents a trans-isoprene unit,

—CH$_2$—C(H$_3$C)=C(H)—CH$_2$— represents a cis-isoprene unit, n is an integer of 11 to 19, Z$^1$ is a —CH$_2$OH group or a CH$_2$OH or —CHO group which is protected by a hydrolyzable or hydrogenolyzable protective group, and either one of R$^1$ and R$^2$ is a hydrogen atom and the other is —S(O)$_m$R$^3$ in which m is an integer of 0 (zero), 1 or 2 and R$^3$ is phenyl, naphthyl, pyridyl or thiazolinyl group, or such group substituted with one lower alkyl and/or halogen substituent.

2. The polyprenyl compound as defined by claim 1, wherein R$^1$ is hydrogen.

3. The polyprenyl compound as defined by claim 1, wherein m is 2.

4. The polyprenyl compound as defined by claim 1, wherein R$^3$ is a phenyl group or a phenyl group bearing one lower alkyl and/or halogen substituent.

5. The polyprenyl compound as defined by claim 1, wherein Z$^1$ is —CH$_2$OH.

6. The polyprenyl compound as defined by claim 1, wherein R$^1$ is a hydrogen atom, R$^2$ is an

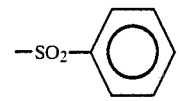

group and Z$^1$ is a —CH$_2$OH group.

7. The polyprenyl compound as defined by claim 1, wherein n is 15.

8. The polyprenyl compound as defined by claim 1 wherein said protective group is a compound of the formula —CH$_2$O—R$^4$ wherein R$^4$ represents a lower alkyl group, an aralkyl group having 7 to 11 carbon atoms, an aliphatic or alicyclic ether residue having 1 to 8 carbon atoms, or a silyl group of the formula —Si(R$_{51}$)(R$_{52}$)(R$_{53}$) in which each of R$_{51}$, R$_{52}$, and R$_{53}$ represents a lower alkyl group, a phenyl group, a tolyl group or a xylyl group.

9. The polyprenyl compound as defined by claim 1 wherein said protective group is —CH$_2$OCH$_3$, —CH$_2$OC$_2$H$_5$, —CH$_2$OC$_3$H$_7$, —CH$_2$OC$_4$H$_9$, —CH$_2$OC$_5$H$_{11}$, —CH$_2$OCH$_2$OCH$_3$, —CH$_2$OCH$_2$OC$_2$H$_5$, —CH$_2$OC$_3$H$_6$OCH$_3$, —CH$_2$OC$_3$H$_6$OC$_2$H$_5$, —CH$_2$OC$_2$H$_4$OC$_2$H$_4$OCH$_3$, —CH$_2$OCH$_2$OC$_2$H$_4$OCH$_3$,

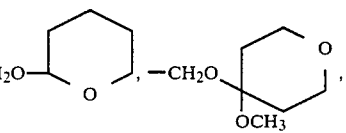

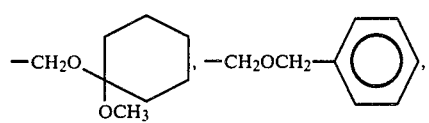

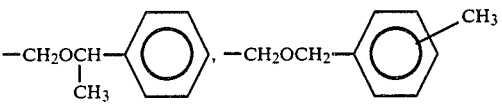

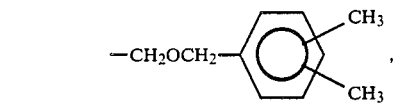

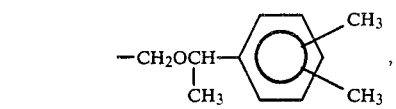

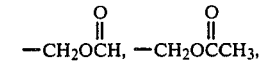

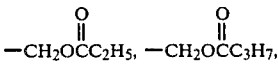

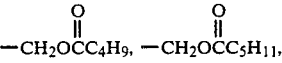

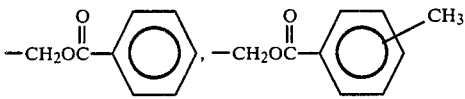

—CH$_2$OSi(CH$_3$)$_3$, —CH$_2$OSi(C$_2$H$_5$)(C$_3$H$_7$)CH$_3$,
—CH$_2$OSi(CH$_3$)$_2$C$_4$H$_9$-t, —CH$_2$OSi(t-C$_4$H$_9$)(C$_6$H$_5$)$_2$,
—CH$_2$OSi(C$_6$H$_5$)$_3$.

10. The polyprenyl compound as defined by claim 1 wherein said protective group is of the formula:
(2) Groups of the formula

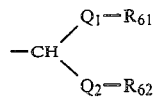

wherein Q$_1$ and Q$_2$ each represents an oxygen or sulfur atom, and R$_{61}$ and R$_{62}$ each represents a lower alkyl group, or when taken together, represent a lower alkylene group.

11. The polyprenyl compound as defined by claim 1 wherein said protective group is of the formula:

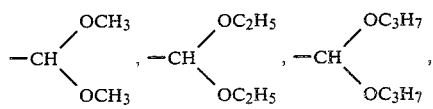

-continued

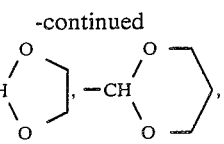

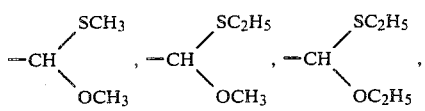

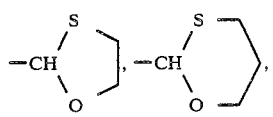

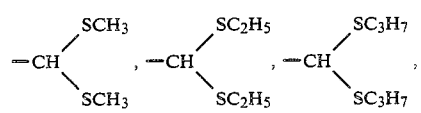

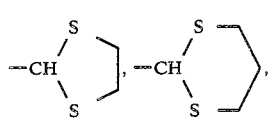

* * * * *